United States Patent
Osakabe et al.

(10) Patent No.: US 12,012,596 B2
(45) Date of Patent: Jun. 18, 2024

(54) TARGET SEQUENCE SPECIFIC ALTERATION TECHNOLOGY USING NUCLEOTIDE TARGET RECOGNITION

(71) Applicant: Tokushima University, Tokushima (JP)

(72) Inventors: Keishi Osakabe, Tokushima (JP); Yuriko Osakabe, Tokushima (JP)

(73) Assignee: Tokushima University, Tokushima (JP)

( * ) Notice: Subject to any disclaimer, the term of this patent is extended or adjusted under 35 U.S.C. 154(b) by 794 days.

(21) Appl. No.: 16/640,521

(22) PCT Filed: Aug. 20, 2018

(86) PCT No.: PCT/JP2018/030607
§ 371 (c)(1),
(2) Date: Feb. 20, 2020

(87) PCT Pub. No.: WO2019/039417
PCT Pub. Date: Feb. 28, 2019

(65) Prior Publication Data
US 2021/0363520 A1    Nov. 25, 2021

(30) Foreign Application Priority Data

Aug. 21, 2017 (JP) ................. 2017-158876
Dec. 8, 2017 (JP) ................. 2017-236518

(51) Int. Cl.
*C12N 15/113* (2010.01)
*C12N 9/22* (2006.01)
*C12N 15/10* (2006.01)
*C12N 15/11* (2006.01)

(52) U.S. Cl.
CPC .............. *C12N 15/111* (2013.01); *C12N 9/22* (2013.01); *C12N 15/102* (2013.01); *C12N 2310/20* (2017.05)

(58) Field of Classification Search
CPC ...... C12N 15/111; C12N 9/22; C12N 15/102; C12N 2310/20
See application file for complete search history.

(56) References Cited

U.S. PATENT DOCUMENTS

| | | | |
|---|---|---|---|
| 2010/0102580 A1 | 4/2010 | Brooks et al. | |
| 2019/0024098 A1 | 1/2019 | Nishida et al. | |
| 2020/0102580 A1 | 4/2020 | Mashimo et al. | |

FOREIGN PATENT DOCUMENTS

| | | | |
|---|---|---|---|
| EP | 3636753 A1 | 4/2020 | |
| JP | 2015-503535 A | 2/2015 | |
| JP | 2017-512481 A | 5/2017 | |
| JP | 6480647 B1 | 3/2019 | |
| WO | 2013/098244 A1 | 7/2013 | |
| WO | 2015/155686 A2 | 10/2015 | |
| WO | 2017/043573 A1 | 3/2017 | |
| WO | 2017/066497 A2 | 4/2017 | |
| WO | 2018/225858 A1 | 12/2018 | |

OTHER PUBLICATIONS

Osakabe et al. Nucleic Acids Research (2021) vol. 49, No. 11, pp. 6347-6363 (Year: 2021).*
International Preliminary Report on Patentability for International Application Patent No. PCT/JP2018/030607, dated Feb. 27, 2020, 10 pages.
International Search Report for International Patent Application No. PCT/JP2018/030607, dated Nov. 6, 2018, 2 pages.
Morisaka H. et al., "Genome editing in mammalian cells by cascade and Cas3", Journal of Investigative Dermatology, May 2017, 137 (5), Suppl. 1, p. S84, 490.
Yang, C. et al., "Comparative genomics reveals diversified CRISPR-Cas systems of globally distributed Microcystis aeruginosa, a freshwater bloom-forming cyanobacterium", Frontiers in Microbiology, 2015, 6: 394, in particular, Fig. 5, 16 pages.
Makarova KS et al., "SnapShot: Class 1 CRISPR-Cas Systems", Cell, 168, Feb. 2017, 168(15), pp. 946-946.e1, in particular, section "Classification".
Makarova K. S. et al., Evolution and classification of the CRISPR-Cas systems. Nat Rev Microbiol, May 9, 2011, vol. 9, No. 6, pp. 467-477, p. 470 and Table 2.
Charpentier E et al., Biogenesis pathways of RNA guides in archaeal and bacterial CRISPR-Cas adaptive Immunity. FEMS Microbiol Rev, May 19, 2015, vol. 39, No. 3, pp. 428-431, p. 433 and Figure 2.
Office Action dated Apr. 20, 2021 in the corresponding Singapore Patent Application No. 11202001471S.
Office Action dated Mar. 23, 2021 in the corresponding Japan Patent Application No. 2019-537609.
Zhao, H. et al., "Crystal Structure of the RNA-guided immune surveillance Cascade complex in *Escherichia coli*", Nature, Nov. 6, 2014, vol. 515, pp. 147-162.
Jackson, R. et al., "Crystal structure of the CRISPR RNA-guided surveillance complex from *Escherichia coli*", Science, Sep. 19, 2014, vol. 345, Issue 6203, pp. 1473-1479.
Mulepati, S. et al., "Crystal structure of a CRISPR RNA-guided surveillance complex bound to a ssDNA target", Science, Sep. 19, 2014, vol. 345, Issue 6203, pp. 1479-1484.
International Search Report for International Patent Application No. PCT/JP2020/011283, dated Jun. 9, 2020, 3 pages.
Mohanraju Prarthana et al.: "Diverse evolutionary roots and mechanistic variations of the CRISPR-Cas systems", Science, vol. 353, No. 6299, Aug. 4, 2016 (Aug. 4, 2016), p. aad5147, XP055791785, US, ISSN: 0036-8075, DOI: 10.1126/science.aad5147.

(Continued)

*Primary Examiner* — J. E. Angell
(74) *Attorney, Agent, or Firm* — Fox Rothschild LLP

(57) ABSTRACT

Provided is a method for targeting a target nucleotide sequence. The method includes introducing, into a cell: (i) CRISPR type I-D related proteins Cas5d, Cas6d, and Cas7d, or nucleic acids encoding these proteins; and (ii) a guide RNA which includes a sequence complementary to said target nucleotide sequence and common repetitive sequences derived from CRISPR gene locus before and after said complementary sequence, or a DNA encoding said guide RNA.

6 Claims, 12 Drawing Sheets
Specification includes a Sequence Listing.

(56) References Cited

OTHER PUBLICATIONS

Makarova Kira S et al: "SnapShot: Class 1 CRISPR-Cas Systems", Cell, Elsevier, Amsterdam NL, vol. 168, No. 5, Feb. 27, 2017 (Nov. 27, 2017), p. 946, XP029932494, ISSN: 0092-8674, DOI: 10.1016/J.CELL.2017.02.018.
Osakabe Keishi et al: "Abstract", Communications Biology, vol. 3, No. 1, 6. Nov. 2020 (Nov. 6, 2020), XP055791658, DOI: 10.1038/s42003-020-01366-6.
Extended European Search Report dated Apr. 23, 2021 in the corresponding European Patent Application No. 18847639.4.
Makarova KS et al., SnapShot: Class 1 CRISPR-Cas Systems,Cell, 168,Feb. 2017, 168(5), pp. 946-946.e1.
Yang C et al.,Comparative genomics reveals diversified CRISPR-Cas systems of globally distributed Microcystis aeru,Front. Microbiol., 2015, 6: 394.
Morisaka, H. et al., Genome editing in mammalian cellsby cascade and Cas3, J. Invest. dermatol., May 2017, vol. 137, p. S84.

\* cited by examiner

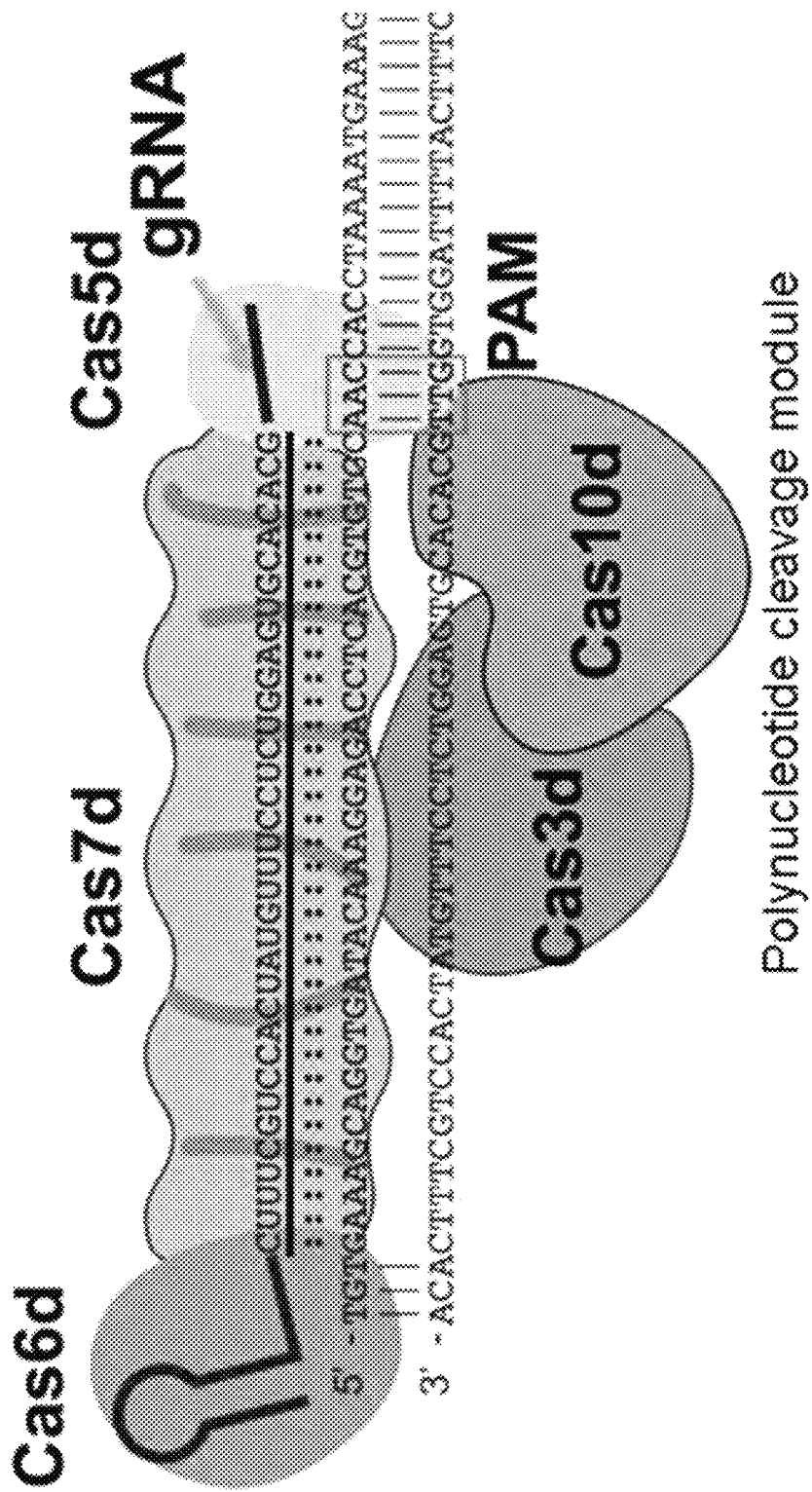
[Fig. 1]

[FIG.2]
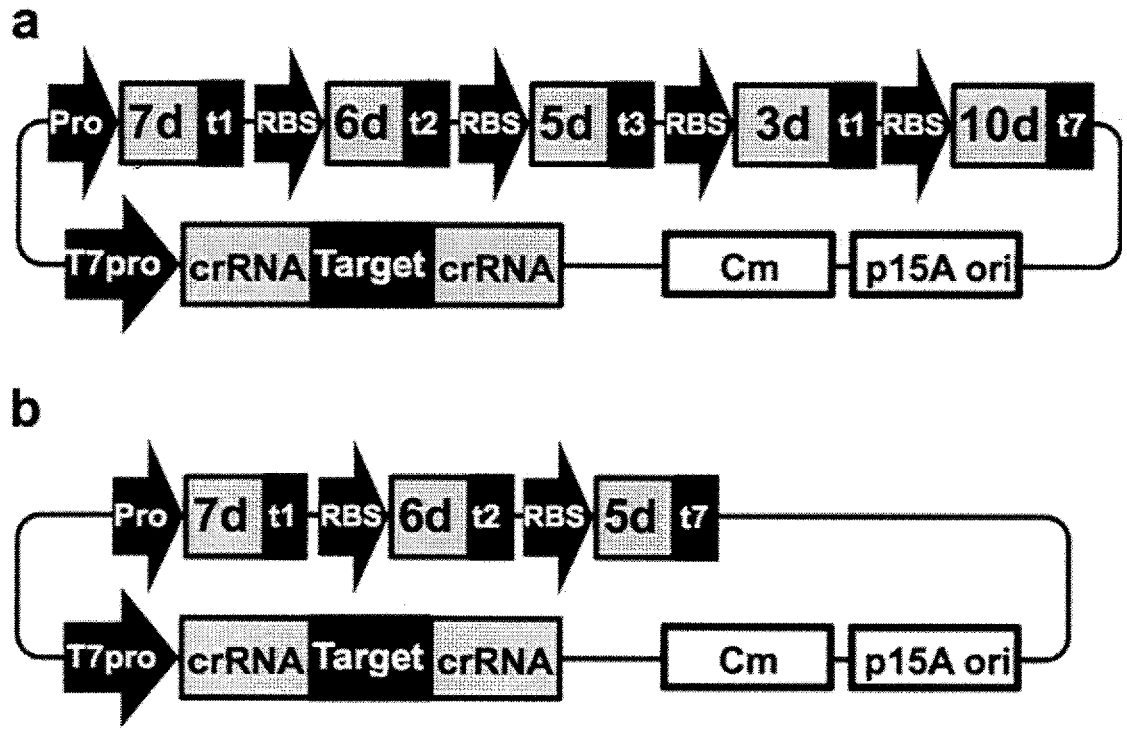
[FIG.3]
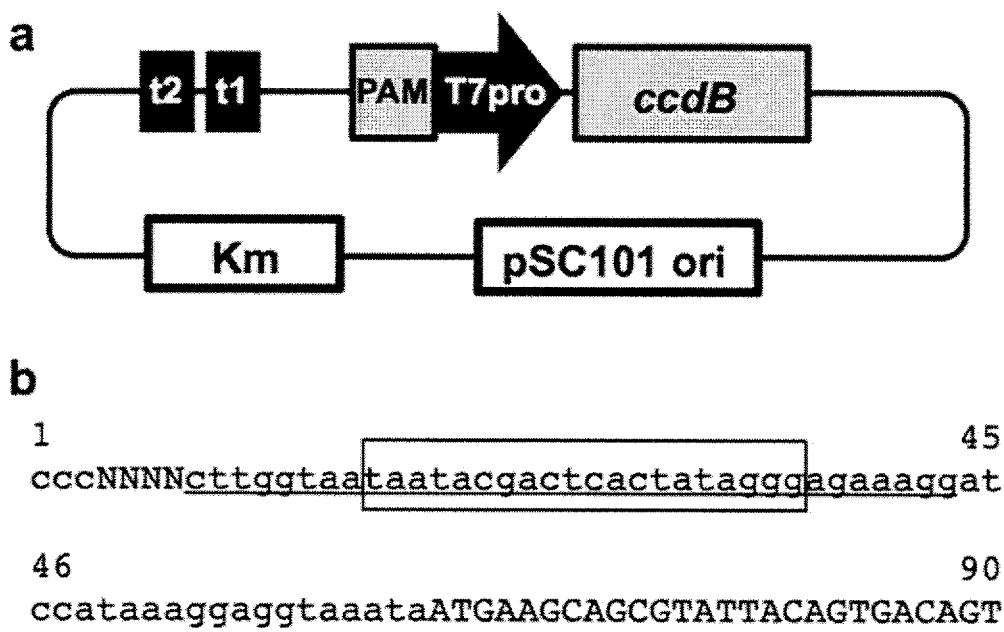

[FIG.4]
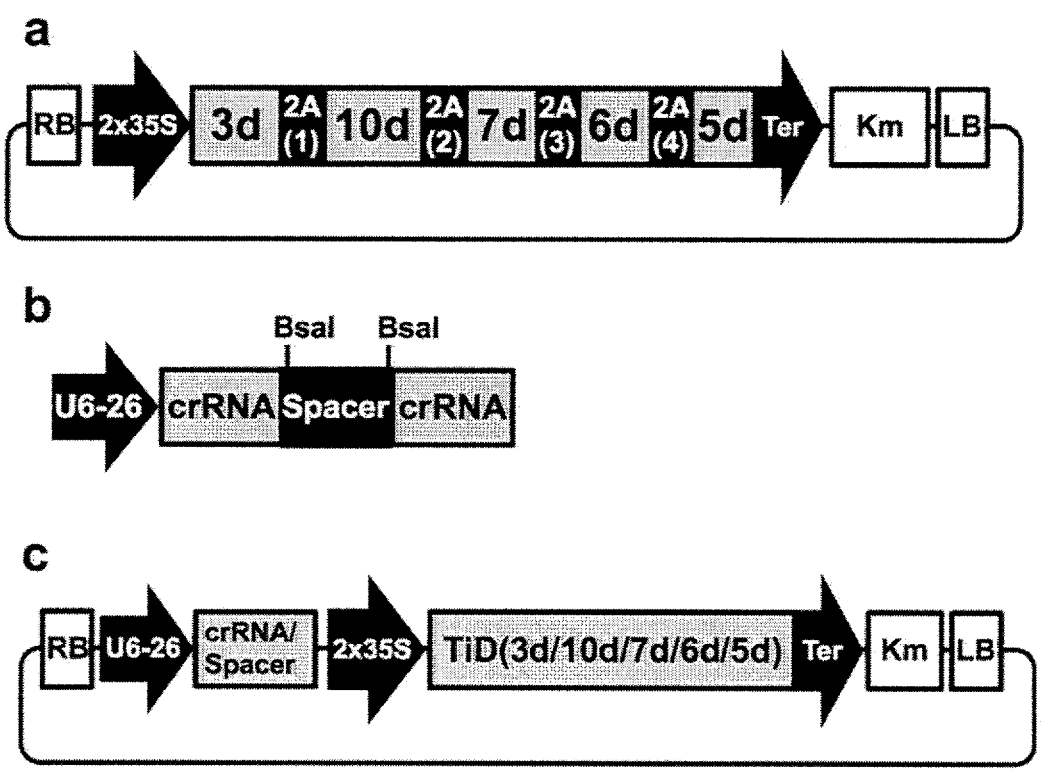

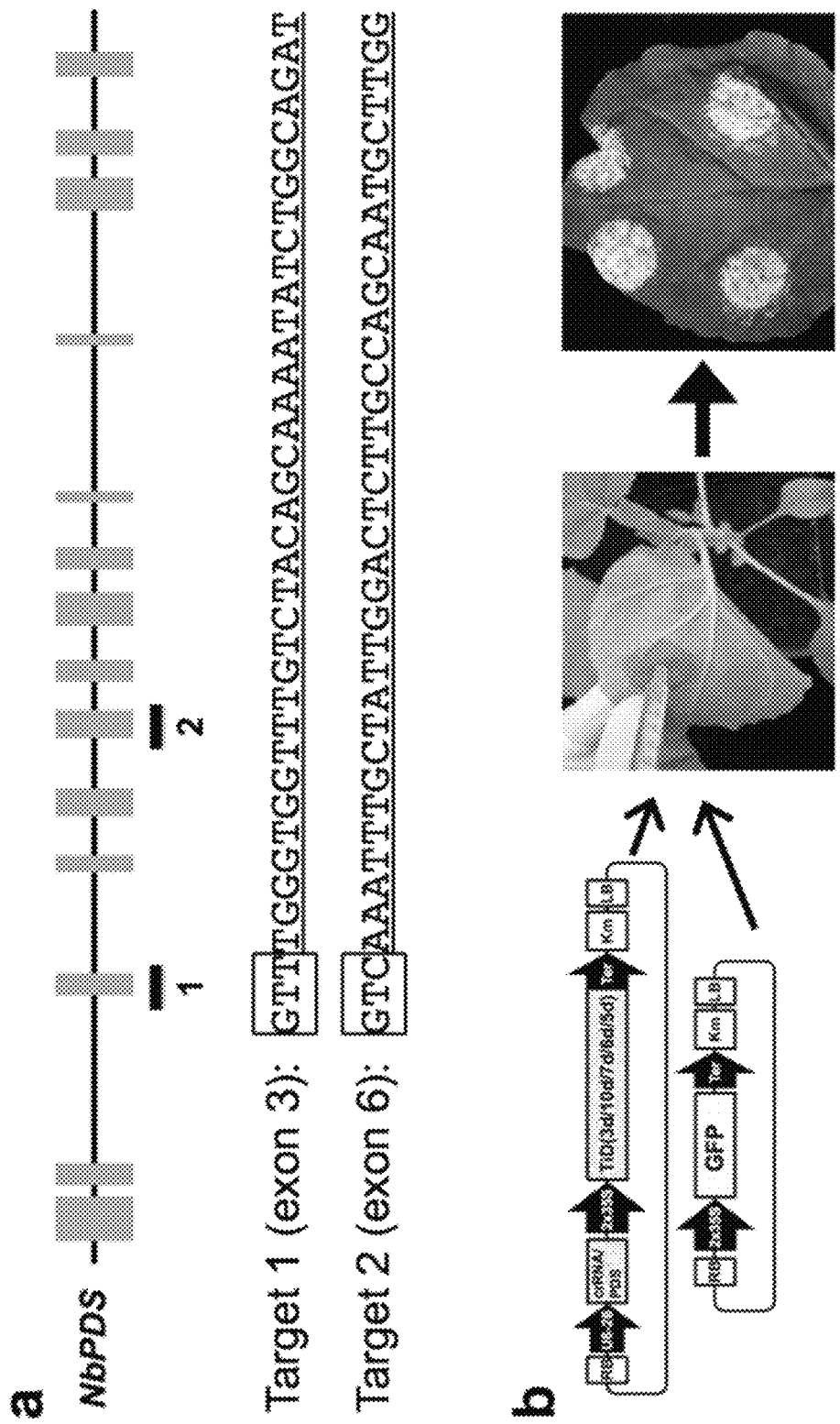

[FIG. 5-2]
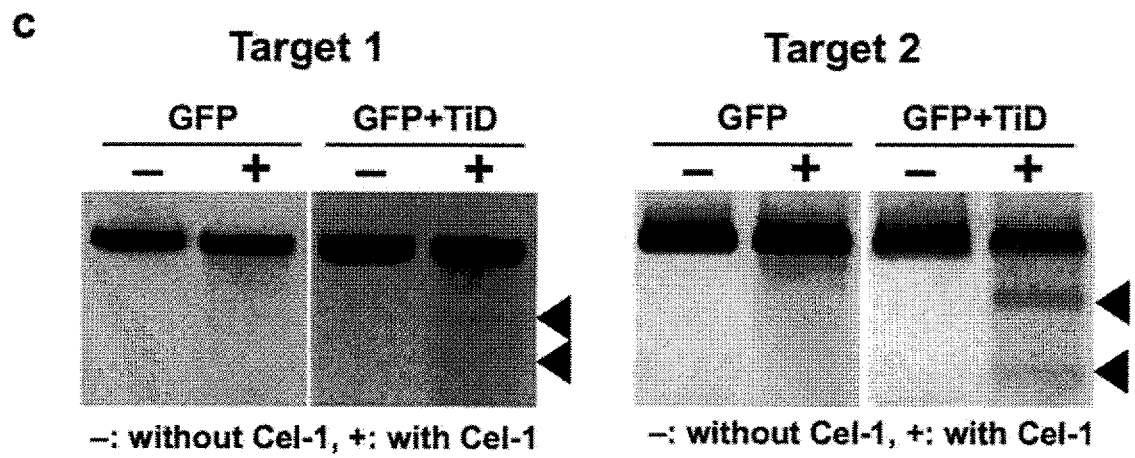

[Fig. 6]
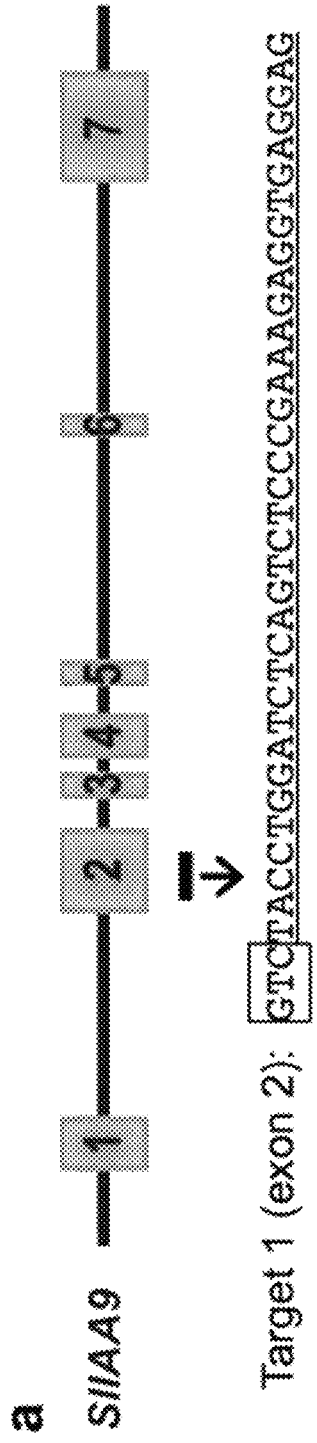
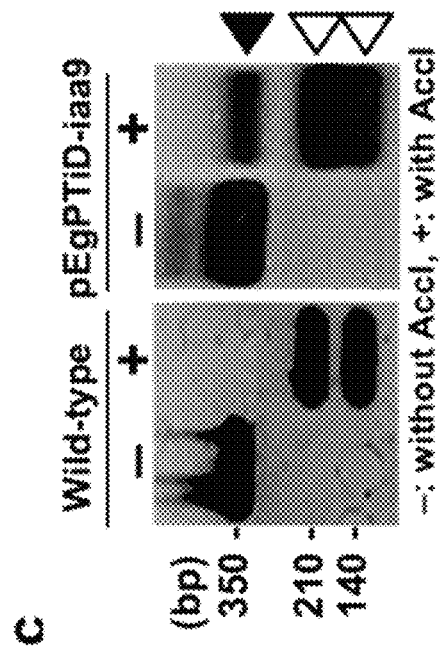
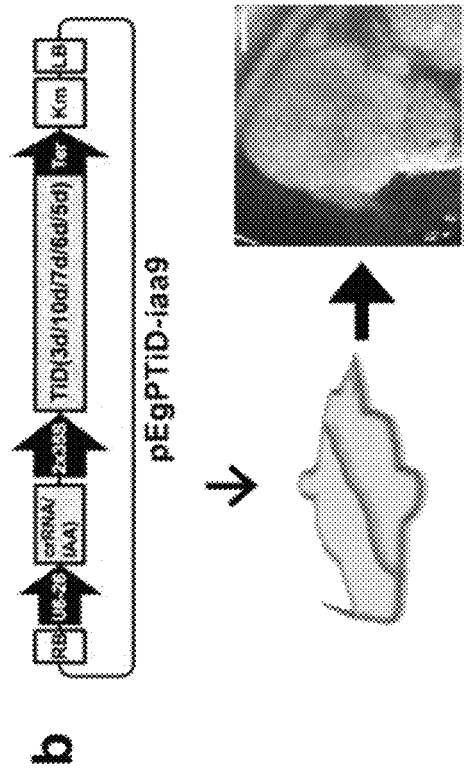

[FIG. 7]

```
                PAM     Target sequence
WT  CTCAGGCTCGGTCTACCTGGATCTCAGTCTCCCGAAAGAGGTGAGGAGACTTGCCC CTCAGGCTCGGTC-ACCTGGATCTCAGTCTCCCGAAAGAGGTGAGGAGACTTGCCC  -1b
    CTCAGGCTCGGTC----TGGATCTCAGTCTCCCGAAAGAGGTGAGGAGACTTGCCC  -4b
    CTCAGGCTCGGTC--CCTGGATCTCAGTCTCCCGAAAGAGGTGAGGAGACTTGCCC  -2b
    CTCAGGCTCGGTCTACCTGGATCTCAGTCTCCCGAAAGAGGTGAGGAGACTTGCCC  +1b CTCAGGCTCGGTCTACCTGGATCTCAGTCTCCCGAAAGAGGTGAGGAGACTTGCCC  +4b
            AAAA
```

[FIG. 8]

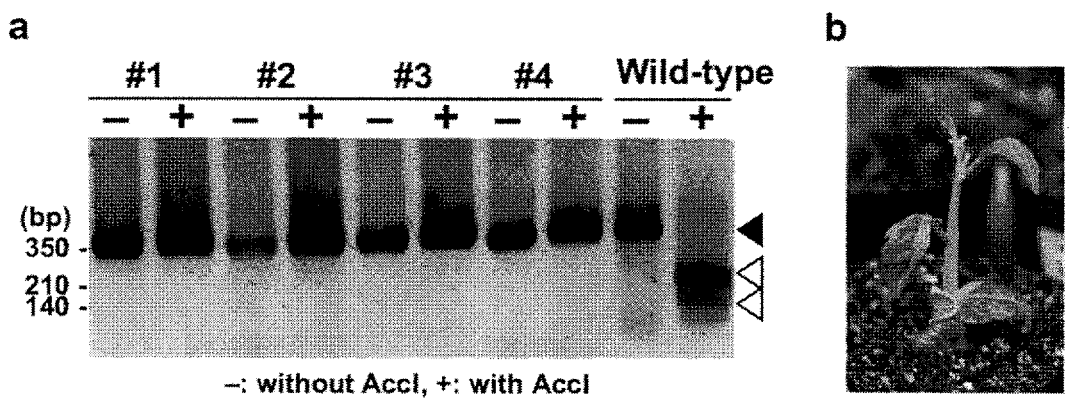

−: without AccI, +: with AccI

[FIG.9]
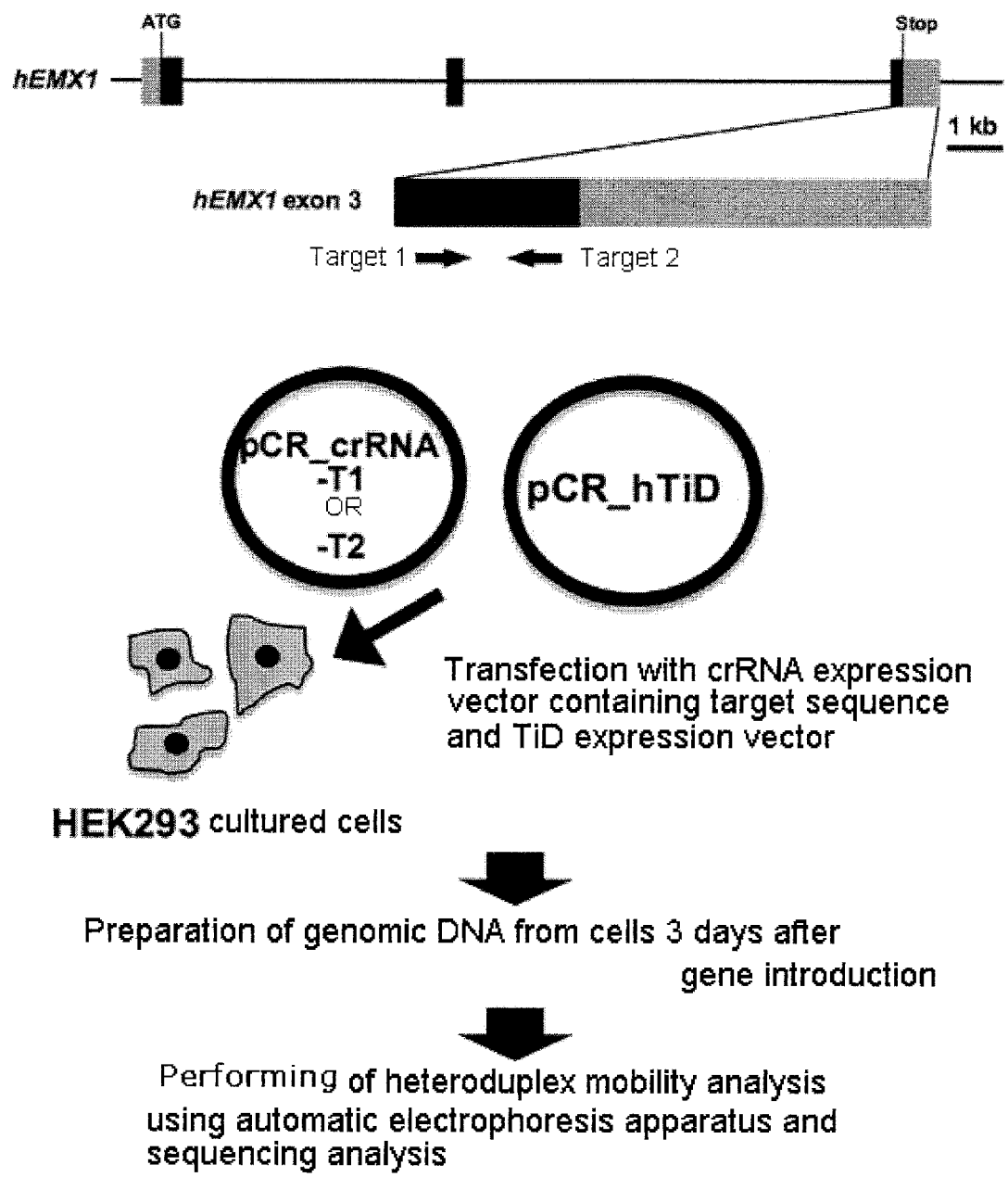

[FIG.10]
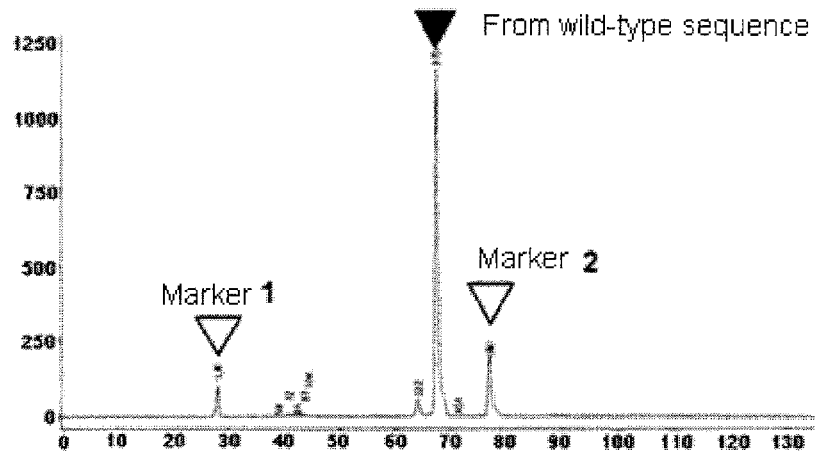
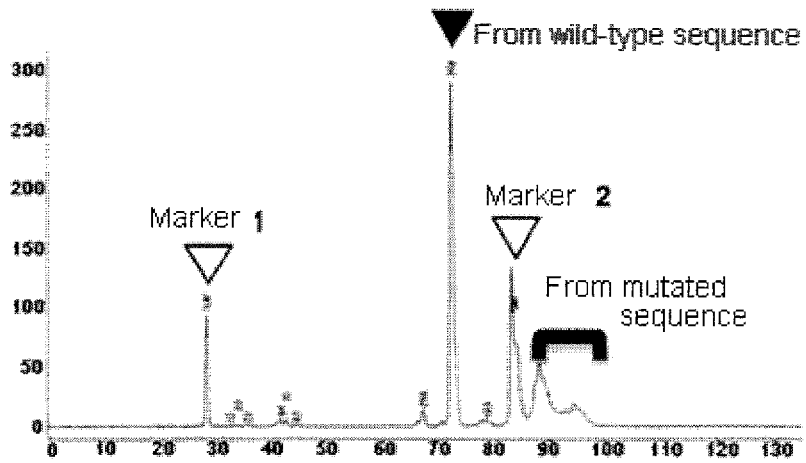
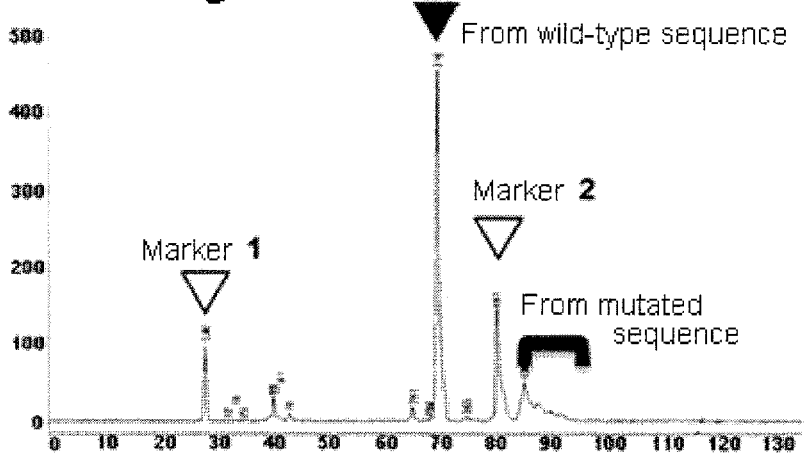

[FIG. 11]
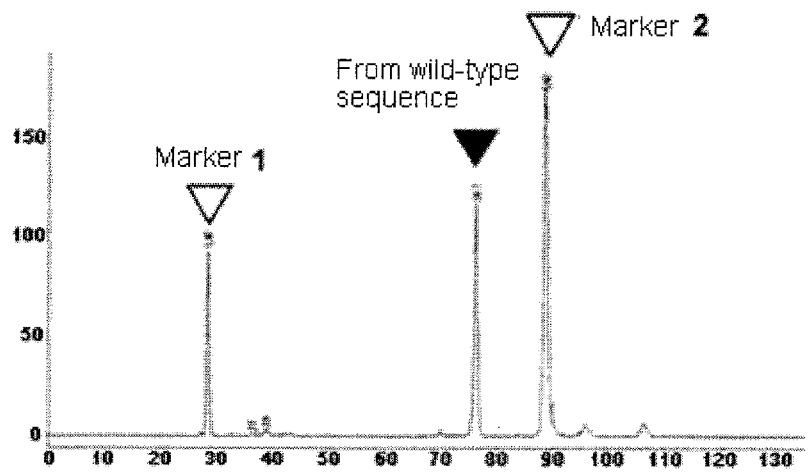
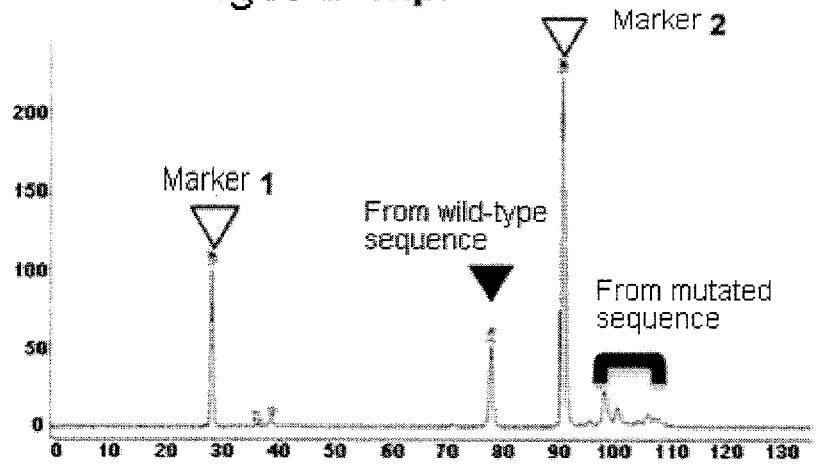
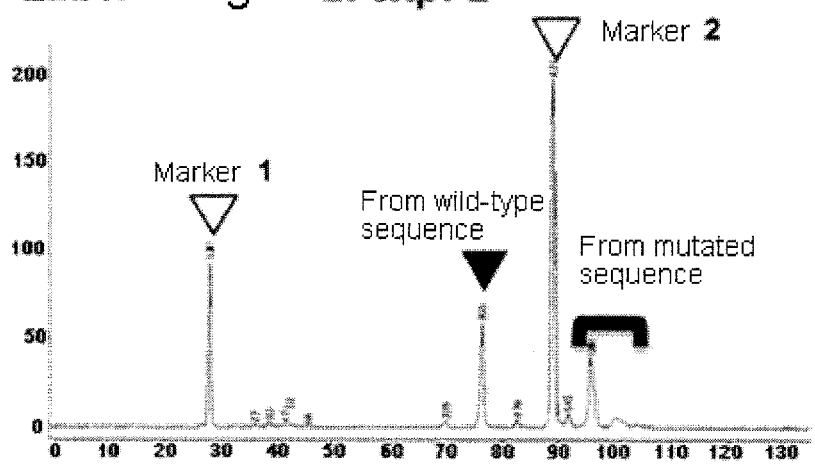

[FIG. 12]

EMX1 Target 1: exp.-1

```
                PAM              Target 1
WT   5'-GGTGTGGTTCCAGAACCGGAGGACAAAGTACAAACGGCAGAAGCTGGA-3'

Mut1 5'-GGTGTGGT---CAGAACCGGAGGACAAAGTACAAACGGCAGAAGCTGGA-3'(3/46)

Mut2 5'-GGTGTGGTT-CAGAACCGGAGGACAAAGTACAAACGGCAGAAGCTGGA-3'(2/46)

Mut3 5'-GGTGTGGT-----------------------AACGGCAGAAGCTGGA-3'(1/46)

Mut4 5'-GGTGTGGa-------------GGACAAAGTACAAACGGCAGAAGCTGGA-3'(1/46)

Mut5 5'-GGTGTG-----AGAACCGGAGGACAAAGTACAAACGGCAGAAGCTGGA-3'(1/46)

Mut6 5'-GGTGTGGT-----AACCGGAGGACAAAGTACAAACGGCAGAAGCTGGA-3'(1/46)
```

EMX1 Target 1: exp.-2

```
                PAM              Target 1
WT   5'-GGTGTGGTTCCAGAACCGGAGGACAAAGTACAAACGGCAGAAGCTGGA-3'

Mut1 5'-GGTGTGGTTC--GAACCGGAGGACAAAGTACAAACGGCAGAAGCTGGA-3'(2/30)

Mut2 5'-GGTGTGGTT-CAGAACCGGAGGACAAAGTACAAACGGCAGAAGCTGGA-3'(1/30)

Mut3 5'-GGTGTGGT-----------------------AACGGCAGAAGCTGGA-3'(1/30)

Mut4 5'-GGTGTGG-------AACCGGAGGACAAAGTACAAACGGCAGAAGCTGGA-3'(1/30)
```

[FIG. 13]

EMX1 Target 2: exp.-1

```
                                    Target 2                PAM
WT    5'-CTGAGTCCGAGCAGAAGAAGAAGGGCTCCCATCACATCAACCGGTGGC-3'

Mut1  5'-CTGAGTCCGAGCAGAAGAAGAAGGGCTCCCATCACAT-AACCGGTGGC-3'(1/40)

Mut2  5'-CTGAGTCCGAGCAGAAGAAGAAGGGCTCCCATCACA--AACCGGTGGC-3'(1/40)

Mut3  5'-CTGAGTCCGAGCAGAAGAAGAAGGGCTCC---------ACCGGTGGC-3'(1/40)

Mut4  5'-CTGAGTCCGAGCAGAAGAAGAAGGGCTCCCATCACAT---CCGGTGGC-3'(1/40)

Mut5  5'-CTGAGTCCGAGCAGAAGAAGAAGGGCTCCCATCACA---ttCGGTGGC-3'(1/40)
```

EMX1 Target 2: exp.-2

```
                                    Target 2                PAM
WT    5'-CTGAGTCCGAGCAGAAGAAGAAGGGCTCCCATCACATCAACCGGTGGC-3'

Mut1  5'-CTGAGTCCGAGCAGAAGAAGAAGGGCTCCCATCACAT-AACCGGTGGC-3'(1/36)

Mut2  5'-CTGAGTCCGAGCAGAAGAAGAAGGGCTCCCATCAC---AACCGGTGGC-3'(1/36)

Mut3  5'-CTGAGTCCGAGCAGAAGA---------------------ACCGGTGGC-3'(1/36)
                      agcgggactccgaaaggagggagacgagctcatccctcgggccttacttgcagctcgca
```

TARGET SEQUENCE SPECIFIC ALTERATION TECHNOLOGY USING NUCLEOTIDE TARGET RECOGNITION

CROSS REFERENCE TO RELATED APPLICATION

The present application claims priority to International Patent Application No. PCT/JP2018/030607 filed Aug. 20, 2018, which also claims priority to Japanese Patent Application No 2017-158876, filed Aug. 21, 2017 and Japanese Patent Application No. 2017-236518, filed Dec. 8, 2017, the entire contents of these applications are incorporated herein for all purposes by this reference.

INCORPORATION-BY-REFERENCE OF A SEQUENCE LISTING

The sequence listing contained in the file "48669-517N01US_Sequence_Listing.txt", created on Feb. 3, 2020, file size 57,561 bytes, is incorporated by reference in its entirety herein.

TECHNICAL FIELD

The present invention relates to a method for targeting a target nucleotide sequence, a method for specifically altering a target nucleotide sequence, and a method for suppressing the expression of a target gene, wherein the nucleotide target recognition of CRISPR (Clustered Regularly Interspaced Short Palindromic Repeats) type I-D system is utilized, and a complex comprising Cas (CRISPR-associated) proteins and a guide RNA used in the methods.

REFERENCE TO AN ELECTRONIC SEQUENCE LISTING

This application contains a Sequence Listing which has been submitted electronically in ASCII format and is hereby incorporated by reference in its entirety. Said text coopy, created on Apr. 17, 2024, is named SeqList-348819-00201.txt; Size: 64,016 bytes in size.

BACKGROUND ART

Bacteria and archaea have CRISPR systems as an adaptive immune system against viruses and heterologous foreign plasmids. The CRISPR system uses a low molecular RNA (referred to as a guide RNA or gRNA) that is complementary to an invading DNA sequence to promote targeting and degradation of the target foreign DNA. At this time, Cas protein that binds to the gRNA to form a complex is required. The CRISPR system includes type I, type II, type III, and Type V systems. In any system, the Cas protein-gRNA complex acts on the target sequence to cause interference with viruses and foreign plasmids. In type II and type V systems, the mechanism of interference involves DNA double-strand breaks on a target DNA by an integrated protein having a protein domain that retains gRNA-binding and a RuvC-like DNA-cleaving protein domain. For the type III system, it has been demonstrated in vitro and in vivo that the interference is caused by cleavage of a target RNA sequence by a complex of five to eight Cas proteins and a gRNA, unlike the type II system.

In recent years, genome editing techniques using the CRISPR type II and type V systems have been developed, wherein Cas9 and Cpf1 are utilized as the Cas protein. Cas9 and Cpf1 require a sequence consisting of about 2 to 5 nucleotides in the vicinity of a target sequence, which is called a protospacer adjacent motif (PAM) sequence, in order to recognize the target DNA. It has been demonstrated in vitro and in vivo that a Cas9-gRNA complex and a Cpf1-gRNA complex are sequence-specific RNA-guided endonucleases that cause DNA double-strand breaks at target sites near PAM sequences.

On the other hand, regarding the CRISPR type I system, a plurality of subtypes have been identified in genomic sequences from various bacteria, and the subtypes have been named type I-A, I-B, I-C, I-D, I-E, I-F, and I-U. Among these subtypes, the type I-E system derived from *Escherichia coli* has been most studied, and it has been demonstrated that a complex consisting of six Cas proteins (Cas3, Cse1, Cse2, Cas7, Cas5, Cas6e) and a gRNA promotes degradation of a target DNA sequence. For the other subtypes excluding a subtype (type I-C), however, Cas protein components, gRNA sequences, PAM sequences that determine target DNAs, etc. required for the interference effect are hardly elucidated. In addition, as techniques using Cas proteins derived from the CRISPR type I system, a method for suppressing the expression of a target gene which comprises using recombinant nucleic acid molecules encoding Cas proteins derived from the CRISPR type I system (Patent Literature 1), and a method for altering a target nucleic acid which comprises using a complex of Cas proteins derived from the CRISPR type I system and other proteins (Patent Literature 2 and Patent Literature 3) have been reported. However, a technique for cleaving and altering a double strand of a target DNA molecule by RNA-guided endonuclease derived from the CRISPR type I system has never been reported.

CITATION LIST

Patent Literature

Patent Literature 1: WO2015/155686
Patent Literature 2: JP-A 2015-503535
Patent Literature 3: WO2017/043573

SUMMARY OF INVENTION

Technical Problems

In the conventional CRISPR type II and type V systems, an RNA molecule to be utilized for targeting is limited to an RNA molecule of about 20 nucleotides preceding or following a PAM sequence of about 2 to 5 nucleotides which determines target specificity. Thus the conventional CRISPR type II and type V systems have problems that there are loci in which a target cannot be designed and that similar sequences may be cleaved. The development of a novel targeting system and a novel RNA-guided endonuclease that does not have the problems is desired.

Solution to Problems

In order to solve the above problems, the present inventors intensively studied. As a result, surprisingly, a novel targeting system and a novel RNA-guided endonuclease that target a longer sequence than the target sequence of the CRISPR type II or type V RNA-guided endonucleases conventionally used in genome editing technology were found from CRISPR type I-D, and then it was found that the novel targeting system and RNA-guided endonuclease can be used in genome editing techniques for allowing alteration on a target nucleotide sequence. Thus the present invention was completed.

That is, the present invention provides:

[1] A method for targeting a target nucleotide sequence, the method comprising introducing into a cell:
 (i) CRISPR type I-D associated proteins Cas5d, Cas6d and Cas7d, or nucleic acids encoding the proteins, and
 (ii) a guide RNA comprising a sequence complementary to the target nucleotide sequence, and common repetitive sequences derived from a CRISPR locus, preceding and following the complementary sequence, or a DNA encoding the guide RNA;

[2] A method for altering a target nucleotide sequence, the method comprising introducing into a cell:
 (i) CRISPR type I-D associated proteins Cas3d, Cas5d, Cas6d, Cas7d and Cas10d, or nucleic acids encoding the proteins, and
 (ii) a guide RNA comprising a sequence complementary to the target nucleotide sequence, and common repetitive sequences derived from a CRISPR locus, preceding and following the complementary sequence, or a DNA encoding the guide RNA;

[3] A method for suppressing the expression of a target gene, the method comprising introducing into a cell:
 (i) CRISPR type I-D associated proteins Cas5d, Cas6d and Cas7d, or nucleic acids encoding the proteins, and
 (ii) a guide RNA comprising a sequence complementary to at least a part of the target gene sequence, and common repetitive sequences derived from a CRISPR locus, preceding and following the complementary sequence, or a DNA encoding the guide RNA;

[4] The method according to any one of [1] to [3], wherein the guide RNA comprises a sequence consisting of 20 to 50 nucleotides which is complementary to the target nucleotide sequence;

[5] The method according to [2] or [4], further comprising introducing a donor polynucleotide into the cell;

[6] The method according to any one of [2], [4] and [5], wherein the alteration is nucleotide deletion, insertion, or substitution;

[7] The method according to any one of [1] to [6], wherein the Cas5d recognizes 5'-GTH-3' (H=A, C, or T) as a protospacer adjacent motif (PAM) sequence;

[8] A complex comprising:
 (i) CRISPR type I-D associated proteins Cas5d, Cas6d and Cas7d, and
 (ii) a guide RNA comprising a sequence complementary to a target nucleotide sequence, and common repetitive sequences derived from a CRISPR locus, preceding and following the complementary sequence;

[9] The complex according to [8], further comprising Cas3d and Cas10d;

[10] The complex according to [8] or [9], wherein the guide RNA comprises a sequence consisting of 20 to 50 nucleotides which is complementary to the target nucleotide sequence;

[11] An expression vector comprising:
 (i) nucleic acids encoding CRISPR type I-D associated proteins Cas5d, Cas6d and Cas7d, and
 (ii) a DNA encoding a guide RNA comprising a sequence complementary to a target nucleotide sequence, and common repetitive sequences derived from a CRISPR locus, preceding and following the complementary sequence;

[12] The expression vector according to [11], further comprising nucleic acids encoding Cas3d and Cas10d;

[13] A DNA molecule encoding the complex according to any one of [8] to [10];

[14] Use of
 (i) CRISPR type I-D associated proteins Cas5d, Cas6d and Cas7d, or nucleic acids encoding the proteins, and
 (ii) a guide RNA comprising a sequence complementary to a target nucleotide sequence, and common repetitive sequences derived from a CRISPR locus, preceding and following the complementary sequence, or a DNA encoding the guide RNA,
 for targeting the target nucleotide sequence;

[15] Use of
 (i) CRISPR type I-D associated proteins Cas3d, Cas5d, Cas6d, Cas7d and Cas10d, or nucleic acids encoding the proteins, and
 (ii) a guide RNA comprising a sequence complementary to a target nucleotide sequence, and common repetitive sequences derived from a CRISPR locus, preceding and following the complementary sequence, or a DNA encoding the guide RNA,
 for altering the target nucleotide sequence;

[16] Use of
 (i) CRISPR type I-D associated proteins Cas5d, Cas6d and Cas7d, or nucleic acids encoding the proteins, and
 (ii) a guide RNA comprising a sequence complementary to at least a part of a target gene sequence, and common repetitive sequences derived from a CRISPR locus, preceding and following the complementary sequence, or a DNA encoding the guide RNA,
 for suppressing the expression of the target gene;

[17] Use according to any one of [14] to [16], wherein the guide RNA comprises a sequence consisting of 20 to 50 nucleotides complementary to the target nucleotide sequence;

[18] Use according to [15] or [17], wherein the alteration is nucleotide deletion, insertion, or substitution;

[19] Use according to any one of [14] to [18], wherein the Cas5d recognizes 5'-GTH-3' (H=A, C, or T) as a protospacer adjacent motif (PAM) sequence;

[20] Use of a complex comprising:
 (i) CRISPR type I-D associated proteins Cas5d, Cas6d and Cas7d, and
 (ii) a guide RNA comprising a sequence complementary to a target nucleotide sequence, and common repetitive sequences derived from a CRISPR locus, preceding and following the complementary sequence, for targeting the target nucleotide sequence;

[21] Use of a complex comprising:
 (i) CRISPR type I-D associated proteins Cas3d, Cas5d, Cas6d, Cas7d and Cas10d and
 (ii) a guide RNA comprising a sequence complementary to a target nucleotide sequence, and common repetitive sequences derived from a CRISPR locus, preceding and following the complementary sequence, for altering the target nucleotide sequence;

[22] Use of the complex comprising:
 (i) CRISPR type I-D associated proteins Cas5d, Cas6d and Cas7d, and
 (ii) a guide RNA comprising a sequence complementary to at least a part of a target gene sequence, and common repetitive sequences derived from a CRISPR locus, preceding and following the complementary sequence, for suppressing the expression of the target gene; and

[23] Use according to any one of [20] to [22], wherein the guide RNA comprises a sequence consisting of 20 to 50 nucleotides complementary to the target nucleotide sequence.

Effects of the Invention

The PAM sequences of the CRISPR type I-D (hereinafter, also referred to as "TiD") system are different from the PAM sequences of the CRISPR type II system and the type V system. Therefore, according to the present invention, the use of the Cas proteins of CRISPR type I-D makes it possible to target loci that cannot be targeted by the conventional genome editing techniques using CRISPR type II or type V RNA-guided endonucleases. Furthermore, the PAM sequences of the CRISPR type I-D-derived RNA-guided endonuclease of the present invention are more frequently found on the genomic sequences of some organisms than the PAM sequences of CRISPR type II and type V. Therefore, according to the present invention, it is possible to target a larger number of gene sequences than the conventional genome editing techniques utilizing the CRISPR type II and type V systems. Furthermore, the present inventors found that a gRNA in the CRISPR type I-D system can target a target sequence having a length of 30 nucleotides or more. On the other hand, a gRNA in the CRISPR type II or type V system can target a sequence having a length of about 20 nucleotides. Thus, the CRISPR type I-D system of the present invention shows more stable binding properties and target specificity than the conventional techniques.

Thus, according to the present invention, it is possible to realize the generation of mutant alleles, control of gene expression by transcriptional activation and inactivation, and epigenomic alteration by targeting of a DNA-modifying/histone-modifying protein domain, on gene regions that cannot be targeted by the conventional techniques.

BRIEF DESCRIPTION OF DRAWINGS

FIG. 1 outlines the component of the CRISPR type I-D system of the present invention and the targeting and cleavage modes on a target sequence. Sequences shown in the FIG. 1 are (from top to bottom): SEQ ID NO:46, SEQ ID NO:47, and SEQ ID NO:48.

FIG. 2 shows the TiD expression vector for *E. coli* genome editing: a) the structure of pEcTiD2 plasmid; b) the structure of pEcTiD3 plasmid, Pro: J23108 synthetic promoter, t1: terminator sequence STOP767, RBS: ribosome binding sequence, t2: terminator sequence STOP768 (1), t3: terminator sequence TOP768 (2), t7: T7 terminator sequence, 7d: Cas7d derived from *Microcystis aeruginosa* (hereinafter, abbreviated as "Ma"), 6d: MaCas6d, 5d: MaCas5d, 3d: MaCas3d, 10d: MaCas10d, T7 pro: T7 promoter, crRNA: TiD-derived CRISPR repeat sequence, Cm: chloramphenicol resistance gene, p15A ori: p15A plasmid-derived replication origin.

FIG. 3 shows the structures of pMW_ccdB and pMW_ccdB-PAM library plasmids: a) the structure of pMW_ccdB, t2: rrnB2 terminator sequence, t1: rrnB1 terminator sequence, PAM: protospacer adjacent motif sequence, T7 pro: T7 promoter, ccdB: ccdB gene, Km: kanamycin resistance gene, pSC101 ori: pSC101 plasmid-derived replication origin; b) the target sequence of pMW_ccdB-PAM plasmid library, wherein random 4 nucleotides are inserted into the NNNN site to obtain a PAM sequence screening library plasmid, a boxed region indicates the T7 promoter, the underlined sequence indicates the TiD target sequence, and capital letters indicate the ccdB locus. The top sequence corresponds to SEQ ID NO:49, the bottom sequence to SEQ ID NO:50.

FIG. 4 shows the TiD expression vector for plant genome editing: a) the structure of pEgPTiD1 plasmid; b) the structure of crRNA expression cassette for plants; c) the structure of pEgPTiD2 plasmid, RB: right border sequence, LB: left border sequence, 2×35S: 2× cauliflower mosaic virus 35S gene promoter and translation enhancer Q sequence, 3d: MaCas3d with a sequence encoding 2×NLS (nuclear localizing signal), 10d: MaCas10d with 2×NLS, 7d: MaCas7d with 2×NLS, 6d: MaCas6d with 2×NLS, 5d: MaCas5d with 2×NLS, 2A (1)-(4): self-cleaving peptide 2A sequences (1)-(4), Ter *Arabidopsis* heat shock protein 18.2 kDa gene terminator, Km: kanamycin resistance gene expression cassette, U6-26: *Arabidopsis* U6 snRNA-26 gene promoter, crRNA: TiD locus-derived CRISPR repeat sequences.

FIG. 5-1 shows the mutagenesis of the tobacco PDS gene using pEgPTiD2-pds: a) target sequences on the tobacco PDS gene, wherein target sequence 1 (SEQ ID NO:51) was selected from the third exon and target sequence 2 (SEQ ID NO:52) was selected from the sixth exon, boxed parts in the target sequences shown in the lower panel indicates the PAM sequences and the underlined parts indicate the target sequences; b) introduction of pEgPTiD2-pds and a GFP expression binary vector by agroinfiltration, wherein agrobacteria carrying pEgPTiD2-pds (1) or pEgPTiD-pds (2) and Agrobacteria carrying a GFP expression binary plasmid were infected by agroinfiltration, and leaf discs in which the GFP expression was observed were excised and used for the analysis of the PDS mutation introduction.

FIG. 5-2 shows the site-directed mutagenesis of the tobacco PDS gene using pEgPTiD2-pds: c) analysis of the PDS mutation introduction by the Cel-1 assay, wherein the genomic DNA was prepared from the leaf discs in which the GFP expression was observed in FIG. 5-*b*), and the presence or absence of mutations was analyzed by the Cel-1 assay. Triangle marks indicate mutated PDS gene fragments that were cleaved by the Cel-1 nuclease.

FIG. 6 shows the mutagenesis of the tomato IAA9 gene using pEgPTiD2-iaa9: a) a target sequence on the tomato IAA9 gene, wherein target sequence 1 (SEQ ID NO:53) was selected from the second exon, a boxed part in the target sequence shown in the lower panel indicates the PAM sequence, and the underlined part indicates the target sequence; b) pEgPTiD2-iaa9 was introduced into a tomato leaf disc by *Agrobacterium* method to obtain transformed callus cells; c) mutation analysis by PCR-RFLP, wherein a region containing the IAA9 target sequence was amplified by PCR from a genomic DNA that was prepared from the transformed callus cells into which pEgPTiD2-iaa9 was introduced, and the mutation analysis was performed by PCR-RFLP using AccI. Open triangles indicate wild type-derived AccI cleavage fragments, and a triangle above the open triangles indicates a mutated fragment that does not undergo AccI cleavage.

FIG. 7 shows mutation analysis by sequencing in pEcTiD2-iaa9 introduced calluses. The top sequence shows the wild type IAA9 sequence (SEQ ID NO:54), and an underlined part indicates the target sequence. Sequences below the wild type IAA9 sequence correspond to: SEQ ID NO:55 (labeled "−1b"), SEQ ID NO:56 (labeled "−4b"), SEQ ID NO:57 (labeled "−2b"), SEQ ID NO:58 (labeled "+1b"), SEQ ID NO:59 (same as SEQ ID NO:58 with "T" inserted at the position indicated in the figure), SEQ ID NO: 60 (labeled "+4b"), and SEQ ID NO: 61 (same as SEQ ID NO: 60 with "AAAA" inserted at the position indicated in the figure). Boxed sequences indicate the PAM sequences. Sites, where mutations occurred, are shown by insertion symbols or hyphens. The hyphen indicates nucleotide deletion.

FIG. 8 shows mutation analysis in a pEcTiD2-iaa9-introduced regenerated plant: a) mutation analysis by PCR-RFLP, wherein open triangles indicate wild type-derived AccI cleavage fragments, and a triangle above the open triangles indicates mutated fragments that do not undergo AccI cleavage; and b) a photograph of a mutation-introduced tomato plant that shows abnormal morphology of true leaves as a result of IAA9 gene disruption.

FIG. 9 shows an experimental scheme of genome editing using the HEK293 cell line.

FIG. 10 shows results of mutation analysis by the heteroduplex mobility analysis. A fragment considered to be derived from a mutated sequence was detected (black key symbol) from the genome of a cell into which a crRNA containing the sequence of target 1 on the EMX1 gene and the TiD genes were introduced.

FIG. 11 shows results of mutation analysis by the heteroduplex mobility analysis. A fragment considered to be derived from a mutated sequence was detected (black key symbol) from the genome of a cell into which a crRNA containing the sequence of target 2 on the EMX1 gene and the TiD genes were introduced.

FIG. 12 shows the sequencing analysis of mutated sequences. White letters in black backgrounds indicate PAM (protospacer adjacent sequence) recognized by TiD. Boxed sequences indicate target sequences. Hyphens (-) indicate nucleotide deletion. A black bold lower case alphabetic character indicates nucleotide insertion. On the right side of each sequence, somatic mutation efficiency (the number of clones in which a mutated sequence was observed/the total number of analyzed clones) is shown. Sequences in FIG. 12 correspond to (from top to bottom): SEQ ID NOs:62-73.

FIG. 13 shows the sequencing analysis of mutated sequences. White letters in black backgrounds indicate PAM (protospacer adjacent sequence) recognized by TiD. Boxed sequences indicate target sequences. Hyphens (-) indicate nucleotide deletion. Black bold lower case alphabetic characters indicate nucleotide insertion. On the right side of each sequence, somatic mutation efficiency (the number of clones in which a mutated sequence was observed/the total number of analyzed clones) is shown. Sequences in FIG. 13 correspond to (from top to bottom): SEQ ID NOs:74-84. SEQ ID NO:85 corresponds to a sequence in which SEQ ID NO:84 is inserted into SEQ ID NO:83 at the position indicated in the figure.

MODE FOR CARRYING OUT THE INVENTION

The present invention provides a genome editing technique utilizing the CRISPR type I-D system. Specifically, among CRISPR type I-D Cas proteins, Cas3d, Cas5d, Cas6d, Cas7d and Cas10d are used in the present invention. In the present invention, the CRISPR type I-D system was found to comprise a target recognition module comprising Cas5d, Cas6d and Cas7d and a polynucleotide cleavage module comprising Cas3d and Cas10d.

Specifically, the action principle of the present invention is as follows.

A complex comprising:
1) a gRNA which is necessary for targeting of a target nucleotide sequence (hereinafter also referred to as "targeting"), comprising a sequence complementary to the target nucleotide sequence and a common repetitive sequence present in a CRISPR type I-D locus,
2) Cas5d which recognizes a PAM sequence present in the vicinity of the target nucleotide sequence,
3) Cas7d which binds to the gRNA of 1) and is necessary for targeting of the target nucleotide sequence, and
4) Cas6d which performs processing of the gRNA of 1), and
5) a complex comprising Cas10d which interacts with the complex comprising 1) to 4) and performs remodeling of the target nucleotide sequence and Cas3d which performs degradation of a polynucleotide are provided to a cell and in the cell,
6) targeting of the target nucleotide sequence by the complex comprising 1) to 4), that is,
7) targeting of the target nucleotide sequence by a complex comprising a mature gRNA that is obtained by processing of the gRNA of 1) by Cas6d of 4), and 2) and 3) is performed, and
8) a polynucleotide on the target nucleotide sequence is cleaved by the complex of 5).

Therefore, the present invention provides a method for targeting a target nucleotide sequence (hereinafter also referred to as "the target sequence-targeting method of the present invention"), a method for altering a target nucleotide sequence (hereinafter referred to as "the target sequence-altering method of the present invention"), and a method for suppressing the expression of a target gene (hereinafter also referred to as "the target gene expression-suppressing method of the present invention"), wherein the CRISPR type I-D system is utilized in the methods. Furthermore, the present invention provides a complex comprising CRISPR type I-D-associated Cas proteins and a gRNA (hereinafter also referred to as "the complex of the present invention"), and a vector comprising a nucleic acid molecule encoding the complex, which are used in the above-mentioned methods of the present invention.

(1) Cell

In the present invention, the cell may be either a prokaryotic cell or a eukaryotic cell, and is not particularly limited. Examples of the cell include bacteria, archaea, yeast, plant cells, insect cells, and animal cells (e.g., human cells, non-human cells, non-mammalian vertebrate cells, invertebrate cells, etc.).

(2) RNA-Guided Endonuclease and Cas Protein

In the present invention, the "RNA-guided endonuclease" means an endonuclease comprising at least one nuclease domain and at least one domain that binds to a gRNA, which is guided to a target nucleotide sequence (or a target nucleotide site) by the gRNA. The RNA-guided endonuclease used in the present invention is an RNA-guided endonuclease derived from CRISPR type I-D, and comprises CRISPR type I-D-associated proteins Cas3d, Cas5d, Cas6d, Cas7d and Cas10d. In the present invention, it was found that Cas5d, Cas6d and Cas7d constitute a "target recognition module" that contributes to target recognition, and Cas3d and Cas10d constitute a "polynucleotide cleavage module" that contributes to cleavage of a polynucleotide. Specifically, the RNA-guided endonuclease used in the present invention comprises the target recognition module comprising Cas5d, Cas6d and Cas7d and the polynucleotide cleavage module comprising Cas3d and Cas10d.

The Cas3d, Cas5d, Cas6d, Cas7d and Cas10d used in the present invention may be derived from any bacterium or archaeum. Examples of the bacterium and the archaeum include *Microcystis aeruginosa, Acetohalobium arabaticum, Ammonifex degensii, Anabaena cylindrica, Anabaena variabilis, Caldicellulosiruptor lactoaceticus, Caldilinea aerophila, Clostridium algicarnis, Crinalium epipsammum, Cyanothece* Sp., *Cylindrospermum stagnale, Haloquadratum walsbyi, Halorubrum lacusprofundi, Methanocaldococ-*

*cus vulcanius, Methanospirillum hungatei, Natrialba asiatica, Natronomonas pharaonis, Nostoc punctiforme, Phormidesmis priestleyi, Oscillatoria acuminata, Picrophilus torridus, Spirochaeta thermophila, Stanieria cyanosphaera, Sulfolobus acidocaldarius, Sulfolobus islandicus, Synechocystis* Sp., *Thermacetogenium phaeum, Thermofilum pendens*, etc. The amino acid sequence and nucleotide sequence information of the Cas proteins are available from public database, for example, NCBI GenBank. In addition, the sequences from novel microbial species can be also obtained from microbial genome data obtained by metagenomic analysis or the like by using the BLAST program. Nucleic acids encoding the Cas proteins may be constructed, for example, by chemical synthesis or the like after selecting optimum codons for translation in a host cell into which the nucleic acids are introduced on the basis of the amino acid sequence information. Use of codons that are frequently used in a host cell makes it possible to increase the expression level of protein. For example, the Cas proteins may be chemically synthesized based on the amino acid sequence information, or produced in a cell by introducing nucleic acids encoding the Cas proteins into the cell via an appropriate vector or the like. Each Cas protein of Cas3d, Cas5d, Cas6d, Cas7d and Cas10d may be a mutant-type Cas protein as long as it retains the function of each Cas protein as described in the action principle of the present invention.

(3) Guide RNA

In the present invention, the guide RNA (gRNA) is a molecule that forms a complex with the target recognition module (Cas5d, Cas6d and Cas7d) to target a target nucleotide sequence together with these Cas proteins. In the present invention, the gRNA binds to Cas7d of the target recognition module. In the present invention, the gRNA binds to a complex comprising Cas5d, Cas6d and Cas7d to guide the complex to the target nucleotide sequence. For example, the gRNA binds to the target recognition module of the RNA-guided endonuclease to guide the RNA-guided endonuclease to the target nucleotide sequence. When the target recognition module is present as a part of a fusion protein other than the RNA-guided endonuclease, the gRNA binds to the target recognition module to guide the fusion protein to the target nucleotide sequence.

The gRNA comprises a sequence complementary to a target sequence so that a base pair may be formed between the gRNA and the target nucleotide sequence, and common repetitive sequences derived from a CRISPR type I-D locus preceding and following (at the 5'-end side and the 3'-end side of) the complementary sequence. The common repetitive sequence parts of gRNA may have at least one hairpin structure. For example, the common repetitive sequence part placed at the 5'-end side of the sequence complementary to a target nucleotide sequence may have a hairpin structure, and the common repetitive sequence part placed at the 3'-end side of the sequence complementary to a target nucleotide sequence may be single-stranded. It the present invention, the gRNA preferably has a hairpin structure.

The common repetitive sequence derived from a CRISPR type I-D locus can be found from a gRNA gene sequence region adjacent to a type I-D gene group by using a tandem repeat search program. The nucleotide length of the common repetitive sequence contained in the gRNA is not particularly limited as long as the gRNA interacts with the target recognition module to target a target nucleotide sequence. For example, each of the common repetitive sequences preceding and following the sequence complementary to a target nucleotide sequence may have a length of about 10 to 70 nucleotides, for example, a length of 30 to 50 nucleotides.

The gRNA can contain a sequence consisting of about 10 to 70 nucleotides, which is complementary to a target nucleotide sequence. The sequence complementary to a target nucleotide sequence contained in the gRNA is preferably a sequence consisting of 20 to 50 nucleotides, more preferably a sequence consisting of 25 to 45 nucleotides, more preferably a sequence consisting of 30 to 40 nucleotides, or even more preferably a sequence consisting of 32 to 37 nucleotides, for example, a sequence consisting of 32 nucleotides, 33 nucleotides, 34 nucleotides, 35 nucleotides, 36 nucleotides, or 37 nucleotides. The sequence specificity of target recognition by the gRNA is more greatly increased as the target sequence that can be targeted is longer. In addition, the Tm value of a base pair formed between the gRNA and the target sequence is higher and thus the stability of target recognition is more greatly increased as the target sequence that can be targeted is longer. Since the length of a sequence that can be targeted by a gRNA for RNA-guided endonucleases (e.g., Cas9 and Cpf1) used in the conventional genome editing techniques is about 20 to 24 nucleotide length, the present invention is excellent in the sequence specificity and the stability as compared with the conventional methods.

(4) Target Nucleotide Sequence

In the present invention, the target nucleotide sequence (also referred to as "the target sequence", as used herein) is any nucleic acid sequence, and is not particularly limited as long as it is a sequence located in the vicinity of a protospacer proximity motif (PAN). The target nucleotide sequence may be a double-stranded DNA sequence, a single-stranded DNA sequence, or an RNA sequence. Examples of DNA include eukaryotic nuclear genomic DNA, mitochondrial DNA, plastid DNA, prokaryotic genomic DNA, phage DNA, and plasmid DNA. In the present invention, the target nucleotide sequence is preferably a double-stranded DNA on the genome. As used herein, the phrase "in the vicinity of" includes both being adjacent to a place and being close to a place. As used herein, the "vicinity" includes both adjacency and neighborhood.

The PAM sequences used for target recognition of CRISPR systems vary depending on the types of CRISPR systems. In the present invention, it was found that the PAM sequence utilized by the CRISPR type I-D system is 5'-GTH-3' (H=A, C or T) (Example 1). Preferably, a sequence located in the vicinity of the 3'-downstream side of the PAM sequence is selected as the target nucleotide sequence. For example, the target nucleotide sequence may be a sequence located in the vicinity of the PAM sequence and present in an intron, a coding region, a non-coding region, or a control region of a target gene. The target gene may be any gene and optionally selected.

The PAM sequences for Cas9 and Cpf1 used in the conventional genome editing techniques are 5'-NGG-3' (N=A, C, G or T) and 5'-TTTV-3' (V=A, C or G), respectively. The appearance frequency of the PAM sequence for TiD (i.e., the number of candidate targets of the CRISPR system) was compared with the appearance frequencies of the PAM sequences for Cas9 and Cpf1 in the genome sequences of higher plants. As a result, it was found that the appearance frequency of the PAM sequence for TiD is the highest, and TiD has a larger number of targets than the conventional genome editing techniques using Cas9 and Cpf1 (Table 1).

TABLE 1

Comparison of PAM sequence number (=number of candidate targets) in genome sequences of higher plants

| Plant species | TiD | Cas9 | Cpf1 |
|---|---|---|---|
| Tomato | $5.99 \times 10^7$ | $5.10 \times 10^7$ | $3.97 \times 10^7$ |
| Strawberry | $1.70 \times 10^7$ | $1.68 \times 10^7$ | $0.99 \times 10^7$ |
| Potato | $5.45 \times 10^7$ | $4.99 \times 10^7$ | $3.71 \times 10^7$ |
| Soybean | $7.20 \times 10^7$ | $6.96 \times 10^7$ | $5.38 \times 10^7$ |
| Hot pepper | $21.58 \times 10^7$ | $20.19 \times 10^7$ | $13.60 \times 10^7$ |
| Poplar | $2.98 \times 10^7$ | $2.77 \times 10^7$ | $2.39 \times 10^7$ |
| Cabbage | $3.67 \times 10^7$ | $3.19 \times 10^7$ | $2.42 \times 10^7$ |
| Beet | $4.11 \times 10^7$ | $4.06 \times 10^7$ | $2.70 \times 10^7$ |
| Bur clover | $3.08 \times 10^7$ | $2.48 \times 10^7$ | $2.31 \times 10^7$ |

(5) The Method of Targeting a Target Sequence of the Present Invention

The method of targeting a target sequence of the present invention is characterized by introducing the target recognition module (Cas5d, Cas6d and Cas7d) and the gRNA into the cell. Specifically, the target sequence-targeting method of the present invention is characterized by introducing into the cell (i) Cas5d, Cas6d and Cas7d, or nucleic acids encoding these proteins, and (ii) the gRNA or a DNA encoding the gRNA. The target sequence-targeting method of the present invention may be performed in vitro or in vivo.

In the method of targeting a target sequence of the present invention, the target recognition module may be introduced into the cell as an isolated complex comprising Cas5d, Cas6d and Cas7d, or each of Cas5d, Cas6d and Cas7d may be introduced into the cell as an isolated single protein. In the target sequence-targeting method of the present invention, the target recognition module may be also introduced into the cell as nucleic acids encoding Cas proteins Cas5d, Cas6d and Cas7d. Examples of the nucleic acid include RNA such as mRNA and DNA.

DNAs encoding the Cas proteins may be contained in, for example, a vector. The DNA sequence is preferably operably linked to a regulatory sequence such as a promoter or terminator. When the cell into which the target recognition module is introduced is a eukaryotic cell, a nuclear localizing signal sequence is preferably added to the DNA encoding the Cas protein. Two or more or all of the DNAs encoding the Cas proteins Cas5d, Cas6d and Cas7d may be contained in a single vector or may be contained in separate vectors. The number of vectors and the kinds and combinations of Cas proteins encoded by the DNAs to be incorporated into each vector are not limited. When two or more DNAs encoding the Cas proteins are contained in a single vector, the DNA sequences may be linked to each other, for example via a sequence encoding a self-cleaving peptide, so as to be polycistronically expressed. The two or more DNAs encoding the Cas proteins may be linked in any order.

The gRNA may be introduced into the cell as an RNA or as a DNA encoding the gRNA. The DNA encoding the gRNA may be contained, for example, in a vector. The DNA sequence is preferably operably linked to a regulatory sequence such as a promoter or a terminator.

The DNAs encoding the Cas proteins and the DNA encoding the gRNA may be contained in the same vector or may be contained in separate vectors. For example, one or more or all of the DNAs encoding Cas5d, Cas6d and Cas7d, and the DNA encoding the gRNA may be contained in a single vector.

The regulatory sequence such as a promoter or a terminator and the nuclear localizing signal sequence are known in the art and can be appropriately selected depending on organism species in which the cell into which the target recognition module and the gRNA are introduced is derived from the organism species. The vector used for introduction may be appropriately selected depending on organism species in which the cell into which the vector is introduced is derived from the organism species, and is not particularly limited. Examples of the vector include plasmid vectors, virus vectors, phagemids, cosmids, artificial/mini-chromosomes, and transposons.

The introduction of the target recognition module and the gRNA into the cell can be performed by various means known in the art. Examples of such means include transfection, e.g., calcium phosphate-mediated transfection, electroporation, liposome transfection, etc., virus transduction, lipofection, gene gun, microinjection, *Agrobacterium* method, Agroinfiltration, and a PEG-calcium method.

The target recognition module and the gRNA may be introduced into the cell simultaneously or sequentially. Cas5d, Cas6d and Cas7d constituting the target recognition module, or nucleic acids encoding these Cas proteins may be introduced into the cell simultaneously or sequentially. For example, the Cas proteins Cas5d, Cas6d and Cas7d synthesized in vitro or in vivo and the gRNA synthesized in vitro or in vivo may be incubated in vitro to form a complex, and the complex may be introduced into the cell.

Upon introduction of the target recognition module and the gRNA, the cell is cultured under suitable conditions for targeting of a target nucleotide sequence. The cell is then cultured under suitable conditions for cell growth and maintenance. The culture conditions may be suitable for the organism species in which the cell into which the target recognition module and the gRNA are introduced is derived from, and can be appropriately determined by a person skilled in the art, for example, based on known cell culture techniques.

According to the method of targeting a target sequence of the present invention, the gRNA binds to Cas7d of the target recognition module to form a complex of the target recognition module and the gRNA. At the same time, the gRNA forms a base pair with the target nucleotide sequence. The target recognition module targets the target nucleotide sequence in a sequence-specific manner by recognizing the PAM sequence present in the vicinity of the target nucleotide sequence. In the target sequence-targeting method of the present invention, Cas10d may be further introduced into the cell.

(6) The Method of Targeting a Target Sequence of the Present Invention

The target sequence-altering method of the present invention is characterized by introducing the RNA-guided endonuclease and the gRNA into the cell. Specifically, the target sequence-altering method of the present invention is characterized by introducing into the cell (i) Cas3d, Cas5d, Cas6d, Cas7d and Cas10d, or nucleic acids encoding the proteins, and (ii) the gRNA or a DNA encoding the gRNA. The target sequence-altering method of the present invention comprises cleaving a nucleotide sequence targeted by the target sequence-targeting method of the present invention with the polynucleotide cleavage module. The target sequence-altering method of the present invention may be performed in vitro or in vivo. In the present invention, the alteration includes deletion, insertion, and substitution of one or more nucleotides, and a combination thereof.

In the method of altering the target sequence of the present invention, in addition to the RNA-guided endonuclease and the gRNA, a donor polynucleotide may be introduced into the cell. The donor polynucleotide comprises at least one donor sequence that contains alteration desired to be introduced into a target site. The donor polynucleotide may comprise, in addition to the donor sequence, sequences having high homology with the upstream and downstream sequences of the target sequence (preferably, sequences substantially identical to the upstream and downstream sequences of the target sequence) at both ends of the donor sequence. The donor polynucleotide may be a single-stranded or double-stranded DNA. The donor polynucleotide can be appropriately designed by a person skilled in the art based on techniques known in the art.

When the donor polynucleotide is absent in the method of altering a target sequence of the invention, cleavage in the target nucleotide sequence may be repaired by non-homologous end joining (NHEJ). NHEJ is known to be error-prone, and deletion, insertion, or substitution of one or more nucleotides, or a combination thereof may occur during the cleavage repair. Thus, the sequence may be altered at the target sequence site, and thereby frameshift or an immature stop codon is induced to inactivate or knock out the expression of the gene encoded by the target sequence region.

When the donor polynucleotide is present in the method of altering a target sequence of the present invention, the donor sequence of the donor polynucleotide is inserted into the target sequence site or replaces the target sequence site by homologous recombination repair (HDR) of the cleaved target nucleotide sequence. As a result, desired alteration is introduced into the target sequence site.

The RNA-guided endonuclease may be introduced into the cell as an isolated complex comprising Cas5d, Cas6d, Cas7d, Cas3d and Cas10d, or each of Cas5d, Cas6d, Cas7d, Cas3d and Cas10d may be introduced into the cell as an isolated single protein. The RNA-guided endonuclease may be also introduced into the cell as nucleic acids encoding the Cas proteins Cas5d, Cas6d, Cas7d, Cas3d and Cas10d. Examples of the nucleic acid include RNA such as mRNA and DNA.

The DNA encoding the Cas protein may be contained in, for example, a vector, and the DNA sequence is preferably operably linked to a regulatory sequence such as a promoter or a terminator. When the cell into which the RNA-guided endonuclease is introduced is a eukaryotic cell, a nuclear localizing signal sequence is preferably added to the DNA encoding the Cas protein. Two or more or all of the DNAs encoding the Cas proteins Cas3d, Cas5d, Cas6d, Cas7d and Cas10d may be contained in a single vector or may be contained in separate vectors. The number of vectors and the kinds and combinations of Cas proteins encoded by the DNAs to be incorporated into each vector are not limited. When two or more DNAs encoding the Cas proteins are contained in a single vector, the DNA sequences may be linked to each other, for example via a sequence encoding a self-cleaving peptide, so as to be polycistronically expressed. The two or more DNAs encoding the Cas proteins may be linked in any order.

The gRNA may be introduced into the cell as an RNA or as a DNA encoding the gRNA. The DNA encoding the gRNA may be contained, for example, in a vector. The DNA sequence is preferably operably linked to a regulatory sequence such as a promoter or a terminator.

The DNAs encoding the Cas proteins and the DNA encoding the gRNA may be contained in the same vector or may be contained in separate vectors. For example, one or more or all of the DNAs encoding Cas3d, Cas5d, Cas6d, Cas7d and Cas10d, and the DNA encoding the gRNA may be contained in a single vector.

The regulatory sequence such as a promoter or a terminator and the nuclear localizing signal sequence are known in the art, and can be appropriately selected depending on the kind of the cell into which the RAN-guided endonuclease and the gRNA are introduced. The vector used for an introduction may be appropriately selected depending on the kind of the cell into which the vector is introduced, and is not particularly limited. Examples of the vector include plasmid vectors, virus vectors, phagemids, cosmids, artificial/mini-chromosomes, and transposons.

The introduction of the RNA-guided endonuclease, the gRNA, and the donor polynucleotide into the cell can be performed by various means known in the art. Examples of such means include transfection, e.g., calcium phosphate-mediated transfection, electroporation, liposome transfection, etc., virus transduction, lipofection, gene gun, microinjection, *Agrobacterium* method, Agroinfiltration, and PEG-calcium method.

The RNA-guided endonuclease, the gRNA, and the donor polynucleotide may be introduced into the cell simultaneously or sequentially. Cas3d, Cas5d, Cas6d, Cas7d and Cas10d constituting the RNA-guided endonuclease, or nucleic acids encoding these Cas proteins may be introduced into the cell simultaneously or sequentially.

Upon introduction of the RNA-guided endonuclease and the gRNA or the RNA-guided endonuclease, the gRNA and the donor polynucleotide, the cell is cultured under suitable conditions for cleavage at the target sequence site. The cell is then cultured under suitable conditions for cell growth and maintenance. The culture conditions may be suitable for the organism species which the cell into which the RNA-guided endonuclease and the gRNA or the RNA-guided endonuclease, the gRNA and the donor polynucleotide are introduced is derived from, and can be appropriately determined by a person skilled in the art, for example, based on known cell culture techniques.

According to the method of altering a target sequence of the present invention, the gRNA forms a base pair with the target nucleotide sequence, and at the same time, the gRNA interacts with the target recognition module of the RNA-guided endonuclease to guide the RNA-guided endonuclease to the target sequence site. Then, the cleavage module of the RNA-guided endonuclease cleaves the sequence at the target sequence site. When the cleaved sequence is repaired, the target sequence is altered. For example, the method of altering a target sequence of the present invention can be used for an alteration of a target nucleotide sequence on the genome. A double-stranded DNA on the genome is cleaved and then altered at a target site by the method of altering a target sequence of the present invention.

(7) The Method of Target Gene Suppression of the Present Invention

The target gene expression-suppressing method of the present invention is characterized by introducing the target recognition module (Cas5d, Cas6d and Cas7d) and the gRNA into the cell. Specifically, the method of target gene suppression of the present invention is characterized by introducing into the cell (i) Cas5d, Cas6d and Cas7d, or nucleic acids encoding the proteins, and (ii) the gRNA or a DNA encoding the gRNA. In the method of target gene suppression of the present invention, at least a part of the target gene sequence is selected as a target nucleotide sequence, and the gRNA containing a sequence complementary to the target sequence is used. The method of target gene suppression of the present invention comprises suppressing the expression of a gene containing the target sequence by binding of a complex of the target recognition module and the gRNA to the target sequence when targeting the target nucleotide sequence by the method of target gene suppression of the present invention. The method of target gene suppression of the present invention may be performed in vitro or in vivo. According to the method of target gene suppression of the present invention, though the target gene sequence is not cleaved, the function of a gene region containing the target sequence or the expression of the gene is inhibited by binding of the complex of the target recognition module and the gRNA to the target nucleotide sequence.

The target recognition module and the gRNA, a method for introducing them into the cell, cell culture at the time of introduction and after introduction, and the like are as described in "(5) The method of targeting a target sequence of the present invention". In the method of target gene suppression of the present invention, Cas10d may be further introduced into the cell.

(8) Complex of the Present Invention

The complex of the present invention comprises the CRISPR type I-D Cas proteins and the gRNA. The present invention particularly provides a complex comprising the target recognition module and the gRNA, and a complex comprising the RNA-guided endonuclease and the gRNA. More specifically, a complex comprising Cas5d, Cas6d, Cas7d and the gRNA, and a complex comprising Cas5d, Cas6d, Cas7d, Cas3d and Cas10d and the gRNA are provided. In addition, a DNA molecule encoding the complex is provided. The complex of the present invention can be used in the method of altering a target sequence, the method of target gene suppression and the method of targeting a target sequence of the present invention. A target sequence on the genome of a cell can be altered by introducing a complex comprising the RNA-guided endonuclease (a complex comprising Cas5d, Cas6d, Cas7d, Cas3d and Cas10d) and the gRNA into the cell to allow the complex to function in the cell. In addition, a target sequence in a cell can be targeted and the expression of a gene encoded by a target sequence region can be suppressed by introducing a complex comprising the target recognition module (a complex comprising Cas5d, Cas6d and Cas7d) and the gRNA into the cell to allow the complex to function in the cell. The complex comprising the target recognition module and the gRNA may further contain Cas10d.

The complex of the present invention can be produced in vitro or in vivo by a conventional method. For example, nucleic acids encoding the Cas proteins constituting the RNA-guided endonuclease or the target recognition module, and the gRNA or a DNA encoding the gRNA may be introduced into a cell to allow the complex to form in the cell.

Examples of the complex of the present invention include, but not limited to, a complex comprising Cas5d (SEQ ID NO: 1), Cas6d (SEQ ID NO: 2) and Cas7d (SEQ ID NO: 3) from *Microcystis aeruginosa*, and a gRNA consisting of a sequence shown by GUUCCAAUUAAUCUUAAGCCCUAUUAGG-GAUUGAAACNNNNNNNNNNNNNNNNNNNNNNNN NNNNNNNNNNNNNGUUCCAAUUAAUCUUAAGCC-CUAUUAGGGAUUGAAAC (SEQ ID NO:6; N is any nucleotide constituting a sequence complementary to a target nucleotide sequence), and a complex comprising Cas 5d (SEQ ID NO: 1), Cas6d (SEQ ID NO: 2), Cas7d (SEQ ID NO: 3), Cas3d (SEQ ID NO: 4), and Cas10d (SEQ ID NO: 5) from *Microcystis aeruginosa*, and a gRNA consisting of a sequence shown by GUUCCAAUUAAUC-UUAAGCCCUAUUAGG-GAUUGAAACNNNNNNNNNNNNNNNNNNNNNNNN NNNNNNNNNNNNNGUUCCAAUUAAUCUUAAGCC-CUAUUAGGGAUUGAAAC (SEQ ID NO:6; N is any nucleotide constituting a sequence complementary to a target nucleotide sequence). In the gRNA sequence, the number of N may be varied within a range of 10 to 70, preferably 20 to 50, more preferably 25 to 45, still more preferably 30 to 40, and still more preferably 32 to 37.

(9) Expression Vector of the Present Invention

The present invention further provides an expression vector containing a nucleic acid encoding the RNA-guided endonuclease comprising Cas3d, Cas5d, Cas6d, Cas7d and Cas10d, and a DNA encoding the gRNA comprising a sequence complementary to a target sequence and common repetitive sequences derived from a CRISPR locus, preceding and following the target sequence, and an expression vector containing nucleic acids encoding CRISPR type I-D-associated proteins Cas5d, Cas6d and Cas7d, and a DNA encoding the gRNA comprising a sequence complementary to a target sequence and common repetitive sequences derived from a CRISPR locus, preceding and following the target sequence.

The vector of the present invention is a vector for introducing the Cas proteins and the gRNA into the cell, as described in "(5) Target sequence-targeting method of the present invention", "(6) Target sequence-altering method of the present invention", and "(7) Target gene expression-suppressing method of the present invention". After the introduction of the vector into the cell, the Cas proteins and the gRNA are expressed in the cell. The vector of the present invention may be also a vector in which the target sequence contained in the gRNA is replaced by any sequence containing a restriction site. Such a vector is used after incorporating a desired target nucleotide sequence into the restriction site. Any sequence may be, for example, a spacer sequence present on a CRISPR type I-D locus or a part of the spacer sequence.

(10) Fusion Protein Comprising the Target Recognition Module of the Present Invention The present invention further provides a fusion protein comprising the target recognition module and a functional polypeptide. When the fusion protein and the gRNA are introduced into a cell, the fusion protein is guided to a target nucleotide sequence or a target gene in the cell by the action of the target recognition module and the gRNA, and the target nucleotide sequence or the target gene is altered or modified by the action of the functional polypeptide. Thus the present invention further provides a method for altering or modifying a target nucleotide sequence or a target gene, which comprises introducing the fusion protein and the gRNA into a cell. Furthermore, the present invention provides a complex comprising the fusion protein and the gRNA.

The functional polypeptide is a polypeptide that exhibits any function to a target sequence and is a polypeptide other than Cas3d and Cas10d. Examples of the functional polypeptide include, but not limited to, restriction enzymes, transcription factors, DNA methylases, histone acetylases, fluorescent proteins; polynucleotide cleavage modules, for example, nucleotide cleavage modules of restriction enzymes; gene expression regulation modules, for example, transcription activation modules and transcription repression modules of transcription factors; and epigenomic modification modules, for example, methylation modules of DNA methylases, and histone acetylation modules of histone acetylases. An example of the fluorescent protein is GFP. For example, a target sequence can be altered by introducing the fusion protein comprising the target recognition module and the polynucleotide cleavage module together with the gRNA into a cell, in the same manner as the method of altering a target sequence of the present invention. For example, a target sequence can be modified to regulate the expression of a target gene by introducing the fusion protein comprising the target recognition module and the gene expression regulation module or the epigenomic modification module together with the gRNA into a cell. For example, the vicinity of a target sequence can be fluorescently labeled by introducing the fusion protein comprising the target recognition module and the fluorescent protein together with the gRNA into a cell.

Hereinafter, examples of the present invention are shown. However, the present invention is not limited to the examples.

EXAMPLES

As one embodiment, a group of genes (Cas3d, Cas5d, Cas6d, Cas7d, Cas10d) derived from the CRISPR type I-D (hereinafter also referred to as "TiD") locus derived from *Microcystis aeruginosa* was cloned and then used. For processing and construction of DNA sequences in Examples, artificial gene chemical synthesis, PCR, restriction enzyme treatment, ligation, or a Gibson Assembly method was used. In addition, the Sanger method or a next generation sequencing method was used to determine nucleotide sequences.

Example 1. Genome Editing in *E. coli*

In this Example, it was demonstrated that the technique of the present invention effectively functions in *E. coli*, which is a typical bacterial model organism.

(1) Construction of TiD Gene Expression Plasmid

A gene group derived from the CRISPR type I-D locus (hereinafter also referred to as "TiD locus") of *Microcystis aeruginosa* (hereinafter also referred to as "*M. aeruginosa*") was cloned. *E. coli* codon-optimized sequences (SEQ ID NOs: 7 to 11) encoding each Cas protein were artificially chemically synthesized based on the amino acid sequence information of Cas5d, Cas6d, Cas7d, Cas3d and Cas10d derived from the TiD locus from *M. aeruginosa*. A DNA fragment comprising a J23108 synthetic promoter (SEQ ID NO: 12) or a synthetic ribosome binding sequence (SEQ ID NO: 13) upstream of each Cas protein-encoding gene and a terminator sequence (SEQ ID NO: 14 to 17) downstream of each Cas protein-encoding gene was ligated into plasmid vector pACYC184 (manufactured by Nippon gene) to construct pEcTiD1. In addition, a CRISPR repeat sequence (crRNA, SEQ ID NO: 18) present in the vicinity of the CRISPR type I-D locus from *M. aeruginosa* was extracted, and a crRNA expression cassette (SEQ ID NO: 20) containing the CRISPR repeat sequence under the control of a T7 promoter (SEQ ID NO: 19) was synthesized. The crRNA expression cassette contained a promoter region sequence of *E. coli* ccdB gene which was a target sequence in this Example. The crRNA expression cassette sequence was incorporated into pEcTiD1 to construct pEcTiD2 (FIG. 2a). Moreover, pEcTiD3 containing Cas5d, Cas6d and Cas7d gene expression cassettes was constructed as a TiD expression plasmid vector for genome editing without DNA double-strand break (FIG. 2b). The promoters, terminators, CRISPR repeat sequence, and crRNA expression cassette sequence used in this Example are shown in Table 2.

TABLE 2

| | |
|---|---|
| J23108 synthetic promoter | 5'-CTGACAGCTAGCTCAGTCCTAGGTATAATGCTA GC-3' (SEQ ID NO: 12) |
| ribosome binding sequence (RBS) | 5'-AATAATTTTGTTTAACTTTAAGAAGGAGATATAC AT-3' (SEQ ID NO: 13) |
| terminator sequence STOP767 | 5'-AGATCCTGTAAAACGACGGCCAGT-3' (SEQ ID NO: 14) |
| terminator sequence STOP768(1) | 5'-CGCCAGGGTTTTCCCAGTC-3' (SEQ ID NO: 15) |
| terminator sequence TOP768(2) | 5' - CGCCAGGGTTTTCCCAGTC-3' (SEQ ID NO: 16) |
| T7 terminator sequence | 5'-TAGCATAACCCCTTGGGGCCTCTAAACGGGTCTTGAGGGG TTTTTTG-3' (SEQ ID NO: 17) |
| CRISPR repeat sequence | 5'-GTTCCAATTAATCTTAAGCCCTATTAGGGATTGAAAC-3' (SEQ ID NO: 18) |
| T7 promoter sequence | 5'-TAATACGACTCACTATAGG-3' (SEQ ID NO: 19) |
| crRNA expression cassette sequence | 5'-GTTCCAATTAATCTTAAGCCCTATTAGGGATTGAAAC ggtaataatacgactcactatagggagaaaggatcGTTCC AATTAATCTTAAGCCCTATTAGGGATTGAAAC-3' (SEQ ID NO: 20) (Upper case letters indicate TiD CRISPR repeat sequence crRNA. Lower case letters indicate a sequence of 35 nucleotides of the promoter region of the ccdB gege, which is the target sequence.) |

(2) Construction of Protospacer Adjacent Motif (PAM) Library

In this Example, a synthetic ccdB gene cassette (SEQ ID NO: 21) (Table 3) in which the T7 promoter sequence is linked upstream of *E. coli* ccdB gene as the target DNA was used. The target sequence of TiD was a sequence of 35 nucleotides comprising the T7 promoter region upstream of the ccdB gene. The synthetic ccdB gene cassette was ligated to a multicloning site in plasmid vector pMW219 (manufactured by Nippon gene) to construct pMW_ccdB1 (FIG. 3a).

The CRISPR system recognizes a protospacer adjacent motif (PAM) sequence located in the vicinity of a target sequence and binds to the target sequence via a gRNA. Since the PAM sequence of *M. aeruginosa* TiD used in this Example was unknown, a PAM sequence library plasmid for determining the PAM sequence of *M. aeruginosa* TiD was constructed. Random four nucleotide sequences were introduced upstream of the T7 promoter of pMW_ccdB1 by using artificial chemical DNA synthesis and PCR (FIG. 3b). The constructed pMW_ccdB-PAM library plasmids were introduced into a ccdB resistant *E. coli* cell line retaining the CcdB resistance (manufactured by Thermo Fisher Scientific), and then the plasmids were prepared.

TABLE 3

SEQ ID NO: 21
Synthetic ccdB gene expression cassette (The underlined sequence indicates the T7 promoter. The uppercase letters indicate the coding region for ccdB gene.)

5'-aggctt<u>taatacgactcactataggg</u>agaaaggatccataaaggaggt aaataatgaagcagcgtattacagtgacagttgacagcgacctaagtcagt tgctcaaggcatatatgatgtcaatatctccggtctggtaagcacaaccat gcagaatgaagcccgtcgtctgcgtgccgaacgctggaaagcggaaaatca ggaagggatggctgaggtcgcccggtttattgaaatgaacggctcttttgc tgacgagaacagggactgggaaATGCAGTTTAAGGTTTACACCTATAAAAG

AGAGAGCCGTTATCGTCTGTTTGTGGATGTACAGAGTGATATTATTGACAC

GCCCGGGCGACGGATGGTGATCCCCCTGGCCAGTGCACGTCTGCTGTCAGA

TAAAGTCTCCCGTGAACTTTACCCGGTGGTGCATATCGGGGATGAAAGCTG

GCGCATGATGACCACCGATATGGCCAGTGTGCCGGTCTCCGTTATCGGGGA

AGAAGTGGCTGATCTCAGCCACCGCGAAAATGACATCAAAAACGCCATTAA

CCTGATGTTCTGGGGAATATAA-3'

(3) Determination of PAM Sequence in *M. Aeruginosa* TiD System

The PAM sequence for TiD was determined by using pEcTiD3-T7 which has inserted the sequence of 35 nucleotides complementary to the T7 promoter region on the pMW_ccdB-PAM library plasmid. The pEcTiD3-T7 was introduced into *E. coli* BL21AI strain (manufactured by Thermo Fisher Scientific) to obtain an *E. coli* host strain for the ccdB gene genome editing. The BL21AI [pEcTiD3-T7] strain expresses Cas5d, Cas6d and Cas7d proteins necessary for target sequence recognition. A Cas5d/Cas6d/Cas7d-crRNA complex recognizes a target sequence adjacent to the appropriate PAM sequence and binds to the target sequence to inhibit the function of the T7 promoter, which is the target sequence, though it does not cleave the target sequence.

The ccdB expression by the pMW-ccdB-PAM introduced into the BL21AI strain is induced in an arabinose-supplemented medium, and BL21AI cells not having the CcdB resistance are killed. When the pMW ccdB-PAM library plasmid is introduced into BL21AI cells into which the TiD expression plasmid has been introduced in advance, the Cas5d/Cas6d/Cas7-crRNA expressed from the pEcTiD3 plasmid binds to the T7 promoter of the pMW_ccdB-PAM library plasmid having an appropriate PAM sequence to be recognized by TiD, thereby production of CcdB protein is inhibited, and thus the *E. coli* cells can grow. From the grown *E. coli* colonies, the pMW_ccdB-PAM library plasmid was prepared, and the PAM sequence was analyzed by sequencing to determine the PAM sequence of *M. aeruginosa* TiD.

The pMW_ccdB-PAM library plasmids, which were prepared in large amounts, were introduced into the BL21AI [pEcTiD3-T7] strain by a chemical competent cell method. The BL21AI cells retaining the pMW ccdB-PAM library plasmid and pEcTiD3-T7 were selected on an LB agar medium containing 25 mg/L chloramphenicol, 25 mg/L kanamycin and 1% glucose. From *E. coli* colonies thus obtained, about 1×10⁷ colonies were collected, washed several times with an LB liquid medium not containing antibiotics and glucose, and then suspended in an LB liquid medium containing 1% arabinose at 1×10⁶ cells/mL. The suspension was cultured with shaking at 37° C. for 2 hours to induce the expression of the crRNA and the ccdB under the control of the T7 promoter by arabinose. Then, 200 μL of the suspension was streaked on an LB agar medium containing 25 mg/L chloramphenicol, 25 mg/L kanamycin and 1% arabinose. After culturing overnight at 37° C., bacterial colonies were collected. From about 500 colonies thus collected, their plasmids were prepared, and the vicinity of the PAM sequence was subjected to sequencing analysis. The PAM sequences of the pMW_ccdB-PAM library plasmids rescued in the presence of the TiD expression plasmid contained sequence 5'-NGTH-3' (N=A, C, G or T; H=A, C or T). The use frequencies of the PAM sequences were 28% for NGTA, 33% for NGTC, and 38% for NGTT. Therefore, it was found that the PAM sequence utilized by TiD was 5'-GTH-3' (H=A, C or T).

(4) Genome Editing in *E. coli*

Plasmids pMW_ccdB-PAMgta, pMW_ccdB-PAMgtc and pMW_ccdB-PAMgtt containing the three types of PAM sequences determined using pEcTiD3-T7 and pMW_ccdB-PAM library plasmids were constructed, and introduced together with pEcTiD2-I7 into the BL21AI strain. The BL21AI cells retaining pMW_ccdB-PAMgta/pEcTiD2-T7, pMW_ccdB-PAMgtc/pEcTiD2-T7 and pMW_ccdB-PAMgtt/pEcTiD2-T7 were selected on an LB agar medium containing 25 mg/L chloramphenicol, 25 mg/L kanamycin and 1% glucose, and then found to contain the plasmid introduced into each bacterial cell by sequencing analysis. Subsequently, the BL21AI cells retaining the correct plasmid were streaked on an LB agar medium containing 25 mg/L chloramphenicol, 25 mg/L kanamycin and 1% arabinose and then cultured overnight at 37° C. As a result, all bacterial cells did not grow, which was probably caused by double-strand DNA break on the plasmid DNA in the presence of Cas3d and Cas10d.

Example 2. Genome Editing in Higher Plants

In this example, as an embodiment of genome editing in higher eukaryotes, it was demonstrated that the technique of the present invention effectively functions in *Nicotiana benthamiana* and *Solanum lycopersicum*.

(1) Construction of Binary Vector for TiD Gene Expression in Higher Plant Cells

According to frequencies in *Arabidopsis* and tobacco, dicotyledon codon-optimized sequences encoding each Cas protein were artificially chemically synthesized based on the amino acid sequence information of Cas5d, Cas6d, Cas7d, Cas3d and Cas10d derived from the TiD locus of *M. aeruginosa*. A DNA fragment comprising a nuclear localizing signal sequence (SEQ ID NO: 22, SEQ ID NO: 23) containing two nuclear localizing signals arranged in tandem 5'-upstream of each of the Cas protein-encoding genes, and a self-cleaving peptide 2A sequence (SEQ ID NOs: 24-28) between the Cas protein-encoding genes was prepared. A promoter sequence (2×35S promoter; SEQ ID NO: 29) comprising tandemly arranged two cauliflower mosaic virus 35S gene promoters and the translation enhancer Q sequence was linked to the 5'-upstream of the five TiD gene fragments fused to each other via 2A peptide sequences, and the *Arabidopsis* heat shock protein 18.2 kDa gene terminator sequence (SEQ ID NO: 30) was linked to the 3'-downstream of the five TiD gene fragments fused to each other via the 2A peptide sequences, and thereby a TiD gene expression cassette was prepared. The TiD gene expression cassette was cloned into binary plasmid vector pCAMBIA2300 to construct pEgPTiD1 (FIG. 4a). For a crRNA expression cassette for plants, a DNA in which a spacer sequence containing two restriction enzyme BsaI sites was placed between two crRNA sequences so that any sequence of 35 nucleotides artificially chemically synthesized could be ligated into the BsaI sites (SEQ ID NO: 31). The *Arabidopsis* U6 snRNA-26 gene promoter sequence (SEQ ID NO: 32) was ligated at 5'-upstream of the crRNA expression cassette sequence, and the poly T sequence was ligated at 3'-downstream of the crRNA expression cassette sequence (FIG. 4b). The crRNA expression cassette for plants was ligated between the RB sequence and the 2×35S promoter of pEgPTidD1 to construct pEgPTiD2, which was used as a TiD gene expression binary plasmid vector for plant genome editing (FIG. 4c). The dicotyledonous codon-optimized sequences encoding each Cas protein to which a nuclear localizing signal is ligated into pEgPTidD1 and pEgPTidD2 are shown in SEQ ID NOs: 33 to 37. The nuclear localizing signal sequence, self-cleaving peptide 2A sequence, promoter, terminator, and crRNA expression cassette sequence used in this Example are shown in Table 4.

TABLE 4-1

| nuclear localizing signal amino acid sequence | DPKKKRKVDPKKKRKVSG (SEQ ID NO: 22) |
|---|---|
| nuclear localizing signal sequence (encoding SEQ ID NO: 22) | 5'-GACCCAAAGAAGAAGCGGAAGGTAGACC CTAAGAAGAAGCGCAAGGTTTCTGGA-3' (SEQ ID NO: 23) |
| self-cleaving peptide 2A amino acid sequence | GSEGRGSLLTCGDVEENPGP (SEQ ID NO: 24) |
| self-cleaving peptide 2A(1) sequence (encoding SEQ ID NO: 24) | 5'-GGCTCTGAGGGCAGAGGCAGCCTGCTGACCT GCGGCGACGTGGAGGAAAACCCTGGCCCT-3' (SEQ ID NO: 25) |
| self-cleaving peptide 2A(2) sequence (encoding SEQ ID NO: 24) | 5'-GGGTCTGAGGGACGCGGCTCCCTGCTCACCT GTGGAGATGTGGAAGAGAACCCAGGCCCC-3' (SEQ ID NO: 26) |
| self-cleaving peptide 2A(3) sequence (encoding SEQ ID NO: 24) | 5'-GGTTCTGAAGGCAGAGGCTCTCTGCTGACAT GTGGGGATGTGGAGGAAAATCCTGGCCCT-3' (SEQ ID NO: 27) |
| self-cleaving peptide 2A(4) sequence (encoding SEQ ID NO: 24) | 5'-GGATCCGAGGGCAGAGGAAGTCTGCTAACAT GCGGTGACGTTGAGGAGAATCCCGGGCCA-3' (SEQ ID NO: 28) |
| 2 × cauliflower mosaic virus 35S gene promoter + Ω sequence | 5'-GCCAACATGGTGGAGCACGACACTCTCGTCT ACTCCAAGAATATCAAAGATACAGTCTCAGA AGACCAAAGGGCTATTGAGACTTTTCAACAA AGGGTAATATCGGGAAACCTCCTCGGATTCC ATTGCCCAGCTATCTGTCACTTCATCAAAAG GACAGTAGAAAAGGAAGGTGGCACCTACAAA TGCCATCATTGCGATAAAGGAAAGGCTATCG TTCAAGATGCCTCTGCCGACAGTGGTCCCAA AGATGGACCCCCACCCACGAGGAGCATCGTG GAAAAAGAAGACGTTCCAACCACGTCTTCAA AGCAAGTGGATTGATGTGAACATGGTGGAGC ACGACACTCTCGTCTACTCCAAGAATATCAA AGATACAGTCTCAGAAGACCAAAGGGCTATT GAGACTTTTCAACAAAGGGTAATATCGGGAA |

TABLE 4-1-continued

```
ACCTCCTCGGATTCCATTGCCCAGCTATCTG
TCACTTCATCAAAAGGACAGTAGAAAAGGAA
GGTGGCACCTACAAATGCCATCATTGCGATA
AAGGAAAGGCTATCGTTCAAGATGCCTCTGC
CGACAGTGGTCCCAAAGATGGACCCCCACCC
ACGAGGAGCATCGTGGAAAAAGAAGACGTTC
CAACCACGTCTTCAAAGCAAGTGGATTGATG
TGATATCTCCACTGACGTAAGGGATGACGCA
CAATCCCACTATCCTTCGCAAGACCCTTCCT
CTATATAAGGAAGTTCATTTCATTTGGAGAG
GCCGGTCTAGAGTATTTTTACAACAATTACC
AACAACAACAAACAACAAACAACATTACAAT
TACTATTTACAATT-3' (SEQ ID NO: 29)
```

TABLE 4-2

| Arabidopsis heat shock protein 18.2 kDa gene terminator | 5'-ATATGAAGATGAAGATGAAATATTTGGTGTGTCAAA TAAAAAGCTTGTGTGCTTAAGTTTGTGTTTTTTCT TGGCTTGTTGTGTTATGAATTTGTGGCTTTTTCTAA TATTAAATGAATGTAAGATCTCATTATAATGAATAA ACAAATGTTTCTATAATCCATTGTGAATGTTTTGTT GGATCTCTTCTGCAGCATATAACTACTGTATGTGCT ATGGTATGGACTATGGAATATGATTAAAGATAAGAT GGGCTCATAGAGTAAAACGAGGCGAGGGACCTATAA ACCTCCCTTCATCATGCTATTTCATGATCTATTTTA TAAAATAAAGATGTAGAAAAAAGTAAGCGTAATAAC CGCAAAACAAATGATTTAAAACATGGCACATAATGA GGAGATTAAGTTCGGTTTACGTTTATTTTAGTACTA ATTGTAACGTGAGAC-3' (SEQ ID NO: 30) |
|---|---|
| crRNA expression cassette for plants | 5'-GTTCCAATTAATCTTAAGCCCTATTAGGGATTGAAA CggagaccctcaattgtcggtctcGTTCCAATTAAT CTTAAGCCCTATTAGGGATTGAAAC-3' (SEQ ID NO: 31) |
| Arabidopsis thaliana U6 snRNA-26 gene promoter sequence | 5'-AAGCTTCGTTGAACAACGGAAACTCGACTTGCCTTC CGCACAATACATCATTTCTTCTTAGCTTTTTTTCTT CTTCTTCGTTCATACAGTTTTTTTTTGTTTTATCAGC TTACATTTTCTTGAACCGTAGCTTTCGTTTTCTTCT TTTTAACTTTCCATTCGGAGTTTTTGTATCTTGTTT CATAGTTTGTCCCAGGATTAGAATGATTAGGCATCG AACCTTCAAGAATTTGATTGAATAAAACATCTTCAT TCTTAAGATATGAAGATAATCTTCAAAAGGCCCCTG GGAATCTGAAAGAAGAGAAGCAGGCCCATTTATATG GGAAAGAACAATAGTATTTCTTATATAGGCCCATTT AAGTTGAAAACAATCTTCAAAAGTCCCACATCGCTT AGATAAGAAAACGAAGCTGAGTTTATATACAGCTAG AGTCGAAGTAGTGATT-3' (SEQ ID NO: 32) |

(2) Genome Editing in *Nicotiana benthamiana*

In Example of tobacco, the phytoene desaturase (PDS) gene was selected as a target sequence for introduction of mutations (FIG. 5-1 a). Target sequence 1 (Target 1, SEQ ID NO: 38) was selected from the third exon in the tobacco PDS gene, and the artificial chemical synthesized DNA of target 1 was ligated into the crRNA expression cassette for plants to construct pEgPTiD2-pds(1). Similarly, target sequence 2 (Target 2, SEQ ID NO: 39) was selected from the sixth exon, and the artificial chemical synthesized DNA of target 2 was ligated into the crRNA expression cassette for plants to construct pEgPTiD2-pds(2). The binary vectors thus constructed were introduced into *Agrobacterium tumefaciens* strain GV2260. Introduction of the TiD expression vector targeting tobacco PDS into tobacco cells was performed by agroinfiltration. *Agrobacterium* cells retaining pEgPTiD2-pds(1) or pEgPTidD2-pds(2) and *Agrobacterium* cells retaining a GFP expression binary vector were separately cultured, and then co-infected to the true leaf of *Nicotiana benthamiana* (FIG. 5-1 b). Three days after the co-infection, a genomic DNA was prepared from a region emitting GFP fluorescence in a leaf disc, and then used as a template to PCR-amplify a 300-500 bp PDS gene fragment containing the target sequence. The PCR amplified fragment was used for the Cel-1 assay to analyze whether a mutation was introduced into the PDS gene. As a control, a tobacco leaf disc into which only the GFP expression binary vector was introduced was used. When only the GFP expression vector was introduced, no mutation was observed on the PDS gene. In contrast, when pEgPTiD2-pds and the GFP expression vector were simultaneously introduced, the introduction of a mutation(s) was observed on each target sequence of the PDS gene (FIG. 5-2 c). Target sequences 1 and 2 are shown in Table 5.

TABLE 5

| Target sequence 1 on tobacco PDS gene (Target 1) | 5'-TGGGTGGTTTGTCTACAGCAAAATATC TGGCAGAT-3' (SEQ ID NO: 38) |
|---|---|
| Target sequence 2 on tobacco PDS gene (Target 2) | 5'-AAATTTGCTATTGGACTCTTGCCAGCA ATGCTTGG-3' (SEQ ID NO: 39) |

(3) Genome Editing in *Solanum lycopersicum*

In Example of tomato, an Aux/IAA transcription factor IAA9 gene was selected as a target sequence for introduction of mutations (FIG. 6a). Target sequence 1 (SEQ ID NO: 40) (Table 6) was selected from the second exon of the tomato IAA9 gene, and the artificial chemical synthesized DNA of target 1 was ligated into the crRNA expression cassette for plants to construct pEgPTiD2-iaa9. The constructed binary vector was introduced into *Agrobacterium tumefaciens* strain GV2260. Introduction of the TiD expression vector targeting the tomato IAA9 gene into tomato cells was performed by an *Agrobacterium* method using a leaf disc derived from tomato cotyledons. Leaf discs co-inoculated with *Agrobacterium* was cultured on an MS solidified medium containing 100 mg/L kanamycin and 1.5 mg/L t-zeatin to obtain calli in which gene introduction of a T-DNA region on pEgPTiD2-iaa9 occurred (FIG. 6b). The recognition sequence for the restriction enzyme AccI exists in the target sequence of IAA9. When a mutation is introduced as a result of genome editing by TiD, the AccI recognition site is disappeared. Thus PCR-restriction enzyme length polymorphism (RFLP) analysis using AccI was performed to analyze mutations that occurred on the target sequence of IAA9. A genomic DNA was prepared from the obtained transformed calli and used as a template to PCR-amplify a region of approximately 300 bases containing the target sequence of IAA9. The PCR fragment was digested with AccI. It was found that the PCR fragment from the callus cultures into which pEgPTiD2-iaa9 was introduced contained a sequence that was not digested by AccI as a result of mutation introduction in the IAA9 target sequence (FIG. 6c). The nucleotide sequence of the PCR fragment from the callus into which pEgPTiD2-iaa9 was introduced was determined. As a result, it was found that nucleotide deletion of 1 to 4 nucleotides was introduced immediately following the PAM sequence on the target sequence of IAA9. (FIG. 7).

Calli into which pEgPTiD2-iaa9 was introduced was further cultured on an MS solidified medium containing 100 mg/L kanamycin and 1.0 mg/L t-zeatin to obtain transformed and regenerated shoots. A genomic DNA was prepared from the regenereated shoots, and used as a template to perform PCR-RFLP analysis with AccI. As shown in FIG. 8a, PCR fragments that were not cleaved with AccI were observed. In other words, the transformed and regenerated shoots into which the IAA9 target sequence was almost 100% mutated were obtained. Of 14 transformed and regenerated shoots, the 13 shoots showed the same results as shown in FIG. 8a. In these regenerated plants, the true leaves were single leaf-shaped, which is one of phenotypes caused by the deficiency of IAA9. Thus, it was shown that a mutation(s) can be introduced with high efficiency by genome editing using TiD.

TABLE 6

| Target sequence on tomato IAA9 gene | 5'-TACCTGGATCTCAGTCTCCCGAAAGAGG TGAGGAG-3' (SEQ ID NO: 40) |
|---|---|

Example 3. Genome Editing in Higher Animals

In this Example, as an embodiment of genome editing in higher animals, it was demonstrated that the technique of the present invention effectively functions in human embryonic kidney cell-derived cell line HEK293.

(1) Construction of Vector for TiD Gene Expression in Higher Animal Cells

Gene sequences encoding each Cas protein were artificially chemically synthesized based on the amino acid sequence information of Cas5d, Cas6d, Cas7d, Cas3d and Cas10d derived from the TiD locus from *M. aeruginosa*. A DNA fragment comprising a nuclear localizing signal sequence (SEQ ID NO: 22, SEQ ID NO: 23) containing two nuclear localizing signals arranged in tandem 5'-upstream of each of the Cas protein-encoding genes, and a the self-cleaving peptide 2A sequence (SEQ ID NOs: 24-28) between the Cas protein-encoding genes was prepared. A cytomegalovirus enhancer+chicken β-actin gene promoter hybrid sequence (CBh promoter; SEQ ID NO: 41) was ligated at 5'-upstream of the five TiD gene fragments fused to each other via the 2A peptide sequences, and a bovine growth hormone gene terminator sequence (bGH terminator; SEQ ID NO: 42) was ligated at 3'-downstream of the five TiD gene fragments fused to each other via the 2A peptide sequences, and thereby a TiD gene expression cassette was prepared. The TiD gene expression cassette was ligated into a pCR8TOPO vector (manufactured by Thermo Fisher Scientific) to construct pCR_hTiD. For a crRNA expression cassette, a DNA in which a spacer sequence containing two restriction enzyme BsaI sites was placed between two crRNA sequences so that any sequence of 35 nucleotides could be ligated was artificially chemically synthesized (SEQ ID NO: 31). The human U6 snRNA gene promoter sequence (SEQ ID NO: 43) as an expression control sequence was ligated at 5'-upstream of the crRNA expression cassette, and the poly T sequence was ligated at 3'-downstream of the crRNA expression cassette. The crRNA expression cassette with the human U6 snRNA gene promoter and the poly T sequence was ligated into a pCR8TOPO vector (manufactured by Thermo Fisher Scientific) to construct pCR_crRNA. The sequences encoding each Cas protein with the nuclear localizing signals in pCR_hTiD are shown as SEQ ID NOs: 33-37. The CBh promoter, bGH terminator, and human U6 snRNA gene promoter sequences are shown in Table 7.

TABLE 7

| | |
|---|---|
| cytomegalo-virus enhancer + universal chicken β-actin gene hybrid promoter | 5'-CGTTACATAACTTACGGTAAATGGCCCGCCTGGCTGAC CGCCCAACGACCCCCGCCCATTGACGTCAATAGTAACG CCAATAGGGACTTTCCATTGACGTCAATGGGTGGAGTA TTTACGGTAAACTGCCCACTTGGCAGTACATCAAGTGT ATCATATGCCAAGTACGCCCCCTATTGACGTCAATGAC GGTAAATGGCCCGCCTGGCATTGTGCCCAGTACATGAC CTTATGGGACTTTCCTACTTGGCAGTACATCTACGTAT TAGTCATCGCTATTACCATGGTCGAGGTGAGCCCCACG TTCTGCTTCACTCTCCCCATCTCCCCCCCCTCCCCACC CCCAATTTTGTATTTATTTATTTTTTAATTATTTTGTG CAGCGATGGGGGCGGGGGGGGGGGGGGCGCGCGCCA GGCGGGGCGGGGCGGGGCGAGGGGCGGGGCGGGCGAG GCGGAGAGGTGCGGCGGCAGCCAATCAGACGGCGCGC TCCGAAAGTTTCCTTTTATGGCGAGGCGGCGGCGGCGG CGGCCCTATAAAAAGCGAAGCGCGCGGCGGGCGGGAGT CGCTGCGACGCTGCCTTCGCCCCGTGCCCCGCTCCGCC GCCGCCTCGCGCCGCCCGCCCCGGCTCTGACTGACCGC GTTACTCCCACAGGTGAGCGGGCGGGACGGCCCTTCTC CTCCGGGCTGTAATTAGCTGAGCAAGAGGTAAGGGTTT AAGGGATGGTTGGTTGGTGGGGTATTAATGTTTAATTA CCTGGAGCACCTGCCTGAAATCACTTTTTTTCAGGTTG GACCGGTGCCACC-3' (SEQ ID NO: 41) |
| bovine growth hormone gene terminator sequence | 5' GCTGATCAGCCTCGACTGTGCCTTCTAGTTGCCAGCCA TCTGTTGTTTGCCCCTCCCCCGTGCCTTCCTTGACCCT GGAAGGTGCCACTCCCACTGTCCTTTCCTAATAAAATG AGGAAATTGCATCGCATTGTCTGAGTAGGTGTCATTCT ATTCTGGGGGGTGGGGTGGGGCAGGACAGCAAGGGGGA GGATTGGGAAGAGAATAGCAGGCATGCTGGGGA-3' (SEQ ID NO: 42) |
| human U6 snRNA gene promoter | 5'-GAGGGCCTATTTCCCATGATTCCTTCATATTTGCATAT ACGATACAAGGCTGTTAGAGAGATAATTGGAATTAATT TGACTGTAAACACAAAGATATTAGTACAAAATACGTGA CGTAGAAAGTAATAATTTCTTGGGTAGTTTGCAGTTTT AAAATTATGTTTTAAAATGGACTATCATATGCTTACCG TAACTTGAAAGTATTTCGATTTCTIGGCTTTATATATC TTGTGGAAAGGACGAAACACC-3' (SEQ ID NO: 43) |

(2) Genome Editing in Cultured Animal Cells

In Example of cultured animal cells, a human embryonic kidney cell-derived cell line (HEK293 cell line) was used, and the EMX1 gene was selected as a target sequence for introduction of mutations. Target 1 (SEQ ID NO: 44) and target 2 (SEQ ID NO: 45) were selected as target sequences in the EMX1 gene, and the artificial chemical synthesized DNA of target 1 and 2 were ligated into the crRNA expression cassette for cultured human cells prepared in above (1) to construct pUC_crRNA-T1 containing target 1 and pUC_crRNA-T2 containing target 2. Constructed plasmids were amplified in E. coli strain HST08 (manufactured by Takara Bio Inc.) and then purified using PureYield (registered trademark) Plasmid Miniprep System (manufactured by Promega Corp.). Among the purified plasmids, a mixture of pCR_hTiD and pUC_crRNA-T1 or a mixture of pCR_hTiD and pUC_crRNA-T2 was introduced into HEK293 cells by transfection. Three days after the introduction of the plasmid vectors, the cells were collected, and a genomic DNA was prepared from them using Blood & Cell Culture DNA Mini Kit (manufactured by Qiagen). Using the genomic DNA thus prepared as a template, the genomic sequence region comprising target 1 or target 2 was amplified by PCR, and mutation analysis was performed by the heteroduplex mobility analysis using an automatic electrophoresis apparatus MultiNA (manufactured by Shimadzu Corporation). Further, the amplified PCR fragment was cloned into pNEB193 vector (manufactured by New England Biolab), and a mutated sequence was identified by sequencing analysis. Somatic mutation efficiency was calculated based on "the number of clones in which a mutated sequence was observed/the total number of clones analyzed". The cell line into which the plasmid had not been introduced, or pCR_hTiD, pUC_crRNA-T1 or pUC_crRNA-T2 had been introduced alone was used as a control to perform mutation analysis in the same manner. An experimental scheme for genome editing using the HEK293 cell line is shown in FIG. 9.

FIG. 10 and FIG. 11 show experimental results obtained when the HEK293 cell line was transfected with the mixture of pCR_hTiD and pUC_crRNA-T1 or the mixture of pCR_hTiD and pUC_crRNA-T2 or when the HEK293 cell line was not transfected with the plasmid (control). As shown in FIG. 10 and FIG. 11, peaks indicating mutations introduced on the target sequence were detected in the HEK293 cell line transfected with the mixture of pCR_hTiD and pUC_crRNA-T1 or the mixture of pCR_hTiD and pUC_crRNA-T2. On the other hand, no peak indicating mutation introduction was detected in the cell line into which the plasmid had not been introduced as a control. Similarly to the cell line into which the plasmid had not been introduced, no peak indicating mutation introduction was detected in the cell line into which pCR_hTiD, pUC_crRNA-T1 or pUC_crRNA-T2 had been introduced alone.

Then, sequence samples in which a peak indicating mutation introduction was detected by heteroduplex mobility analysis were cloned into a plasmid vector and analyzed by sequencing. As a result, as shown in FIG. 12 and FIG. 13, it was found that deletion and/or insertion mutations were introduced on target1 and target 2.

TABLE 8

Target sequences on human EMX 1 gene

| Target 1 | 5'-CCAGAACCGGAGGACAAAGTACAAACGGCAGAAGC-3' (SEQ ID NO: 44) |
|---|---|
| Target 2 | 5'-GATGTGATGGGAGCCCTTCTTCTTCTGCTCGGACT-3' (SEQ ID NO: 45) |

INDUSTRIAL APPLICABILITY

According to the present invention, it is possible to target a gene sequence that cannot be targeted by the conventional genome editing technique using CRISPR type II or type V-derived RNA-guided endonuclease. Specifically, according to the present invention, it is possible to generate mutant alleles, control gene expression by transcriptional activation and inactivation, and realize epigenomic alteration by targeting of a DNA-modifying/histone-modifying protein domain, on gene regions that cannot be targeted by the conventional techniques.

SEQUENCE LISTING FREE TEXT

SEQ ID NO: 1; *Microcystis aeruginosa* Cas5d amino acid sequence
SEQ ID NO: 2; *Microcystis aeruginosa* Cas6d amino acid sequence
SEQ ID NO: 3; *Microcystis aeruginosa* Cas7d amino acid sequence
SEQ ID NO: 4; *Microcystis aeruginosa* Cas3d amino acid sequence
SEQ ID NO: 5; *Microcystis aeruginosa* Cas10d amino acid sequence SEQ ID NO: 6; TiDcrRNA containing direct repeat (37b) and spacer (35b of N). N is any nucleotide constituting a complementary sequence to a target nucleotide sequence.
SEQ ID NO: 7; Cas5d nucleotide sequence for expression in *Escherichia coli*
SEQ ID NO: 8; Cas6d nucleotide sequence for expression in *Escherichia coli*
SEQ ID NO: 9; Cas7d nucleotide sequence for expression in *Escherichia coli*
SEQ ID NO: 10; Cas3d nucleotide sequence for expression in *Escherichia coli*
SEQ ID NO: 11; Cas10d nucleotide sequence for expression in *Escherichia coli*
SEQ ID NO: 12; J23108 synthesis promoter
SEQ ID NO: 13; Ribosomal binding sequence
SEQ ID NO: 14; Terminator sequence STOP767
SEQ ID NO: 15; Terminator sequence STOP768 (1)
SEQ ID NO: 16; Terminator sequence TOP768 (2)
SEQ ID NO: 17; T7 terminator sequence
SEQ ID NO: 18; CRISPR repeat sequence
SEQ ID NO: 19; T7 promoter sequence
SEQ ID NO: 20; crRNA expression cassette
SEQ ID NO: 21; Synthesis cccdB gene expression cassette
SEQ ID NO: 22; Nuclear localizing signal (NLS) amino acid sequence
SEQ ID NO: 23; NLS nucleotide sequence
SEQ ID NO: 24; Self-cleaving peptide 2A amino acid sequence
SEQ ID NO: 25; Self-cleaving peptide 2A(1) coding sequence
SEQ ID NO: 26; Self-cleaving peptide 2A(2) coding sequence
SEQ ID NO: 27; Self-cleaving peptide 2A(3) coding sequence
SEQ ID NO: 28; Self-cleaving peptide 2A(4) coding sequence
SEQ ID NO: 29; 2× cauliflower mosaic virus 35S gene promoter+omega sequence
SEQ ID NO: 30; *Arabidopsis* shock protein 18.2 kDa gene terminator
SEQ ID NO: 31; crRNA expression cassette
SEQ ID NO: 32; *Arabidopsis* U6 snRNA-26 gene promoter sequence
SEQ ID NO: 33; 2×NLS+Cas5d
SEQ ID NO: 34; 2×NLS+Cas6d
SEQ ID NO: 35; 2×NLS+Cas7d
SEQ ID NO: 36; 2×NLS+Cas3d
SEQ ID NO: 37; 2×NLS+Cas10d
SEQ ID NO: 38; Target sequence 1 on tobacco PDS gene
SEQ ID NO: 39; Target sequence 2 on tobacco PDS gene
SEQ ID NO: 40; Target sequence on tomato IAA9 gene
SEQ ID NO: 41; Cytomegalovirus enhancer+universal chicken beta-actin gene hybrid promoter
SEQ ID NO: 42; Bovine-derived growth hormone gene terminator sequence
SEQ ID NO: 43; Human U6 snRNA gene promoter
SEQ ID NO: 44; Target 1 sequence on human EMX1 gene
SEQ ID NO: 45; Target 2 sequence on human EMX1 gene

The invention claimed is:

1. A method for altering a target nucleotide sequence, the method comprising
   (a) introducing into a cell:
      (i) one or more expression cassettes comprising nucleic acids encoding CRISPR type I-D associated proteins Cas3d, Cas5d, Cas6d, Cas7d and Cas10d, and
      (ii) a guide RNA comprising (1) a sequence complementary to the target nucleotide sequence and (2) common repetitive sequences derived from a CRISPR locus, preceding and following the complementary sequence, or a DNA encoding the guide RNA,
   wherein the target nucleotide sequence is a double-stranded DNA; and
   (b) cleaving the target nucleotide sequence using Cas3d and Cas10d, whereby repair of the cleaved target nucleotide sequence results in altering the target nucleotide sequence.

2. The method according to claim 1, further comprising introducing a donor polynucleotide into the cell.

3. The method according to claim 1, wherein the target nucleotide sequence is altered by nucleotide deletion, insertion, or substitution.

4. The method according to claim 1, wherein one or more expression vectors are introduced into the cell, the one or more expression vectors comprising:
   (i) the one or more expression cassettes comprising nucleic acids encoding CRISPR type I-D associated proteins Cas3d, Cas5d, Cas6d, Cas7d and Cas10d, and
   (ii) a DNA encoding a guide RNA comprising a sequence complementary to the target nucleotide sequence, and common repetitive sequences derived from a CRISPR locus, preceding and following the complementary sequence, and
   thereby the nucleic acids encoding the Cas proteins and the DNA encoding the guide RNA are introduced into the cell.

5. The method according to claim 1, wherein the guide RNA comprises a sequence consisting of 20 to 50 nucleotides which is complementary to the target nucleotide sequence.

6. The method according to claim 1, wherein the Cas5d recognizes 5'-GTH-3' (H=A, C, or T) as a protospacer adjacent motif (PAM) sequence.

* * * * *

SEQUENCE LISTING

```
<160> NUMBER OF SEQ IDS NOS: 45

<210> SEQ ID NO 1
<211> LENGTH: 224
<212> TYPE: PRT
<213> ORGANISM: Microcystis aeruginosa

<400> SEQUENCE: 1

Met Val His Ile Tyr Ser Cys Gln Leu Glu Leu His Asp Ser Leu Tyr
1               5                   10                  15

Tyr Ala Thr Arg Glu Ile Gly Arg Leu Tyr Glu Ser Glu Pro Val Ile
            20                  25                  30

His Asn Tyr Ala Leu Cys Tyr Ala Leu Gly Leu Val Asn Ser Asp Ser
        35                  40                  45

Tyr Arg Tyr Phe Cys Ser Glu Gln Ile Pro Gln Tyr Gln Glu His Leu
    50                  55                  60

Asn Pro Leu Asn Glu Glu Lys Ile Tyr Val Thr Pro Ala Arg Ala Ile
65                  70                  75                  80

Ala His Thr Ala Val Leu Asn Thr Trp Lys Tyr Ala Asn Asn Asn Tyr
                85                  90                  95

His Val Glu Met Glu Lys Thr Gln Lys Asn Ile Pro Ser Phe Gly Arg
            100                 105                 110

Ala Lys Glu Ile Ala Pro Glu Ser Ile Phe Glu Cys Phe Ile Ile Ser
        115                 120                 125

His His Pro Leu Gln Leu Pro Lys Trp Ile Arg Leu Gly Lys Trp Met
    130                 135                 140

Ser Lys Ala Glu Val Lys Leu Thr Glu Leu Ser Leu Ser Lys Gln Lys
145                 150                 155                 160

Glu Asp Leu Phe Ile Tyr Pro Tyr Pro Leu Asn Pro Leu Asp Val Met
                165                 170                 175
```

```
Phe Thr His Gln Val Ile Gly Tyr Asp Val Ile Asn Met Pro Pro Val
            180                 185                 190

Ser Leu Ile Arg Asn Val Arg Met Arg Gly Glu Tyr Tyr Gln Ile Ser
        195                 200                 205

Asp Arg Pro Asp Leu Lys Ile Pro Ala Arg Leu Ser Tyr His Phe Gly
    210                 215                 220

<210> SEQ ID NO 2
<211> LENGTH: 277
<212> TYPE: PRT
<213> ORGANISM: Microcystis aeruginosa

<400> SEQUENCE: 2

Met Pro Tyr Ser Leu Val Leu Asn Leu Thr Pro Arg Ser Pro Ile Tyr
1               5                   10                  15

Pro Asn Phe Leu Thr Gly Arg His Leu His Ala Leu Phe Leu Thr Leu
            20                  25                  30

Val Ser Ser Val Asp Gln Glu Leu Gly Asn Ile Leu His Thr Ala Glu
        35                  40                  45

Ala Asp Lys Ala Phe Thr Leu Ser Pro Leu Gln Met Gln Ser Gly Gly
    50                  55                  60

Lys Thr Ile Asn Ser Pro Gln Trp Arg His Glu Arg Glu Ile Ala Ser
65                  70                  75                  80

Glu Thr Pro Cys Trp Trp Arg Ile Ser Leu Leu Asp Asp Arg Leu Phe
                85                  90                  95

Gly Lys Leu Thr Ser Leu Trp Leu Asn Leu Asn Pro Lys Gln Pro Trp
            100                 105                 110

His Leu Gly Ser Ala Asp Leu Val Ile Thr Ser Val Leu Ala Thr Pro
        115                 120                 125

Gln Ser Val Gln Pro Trp Ala Asn Ser Cys Thr Tyr Gln Tyr Leu Tyr
    130                 135                 140

Glu Asn Ala Ser Glu Thr Asn Arg Glu Phe Asp Phe Leu Phe Ala Thr
145                 150                 155                 160

Pro Val Thr Phe Arg Gln Gly Lys Phe Asp Ser Ala Leu Pro Thr Arg
                165                 170                 175

Glu Leu Val Phe Asn Ser Leu Leu Gly Arg Trp Asn Arg Tyr Ser Gly
            180                 185                 190

Ile Pro Phe Asp Ser Ile Ala Leu Glu Ser Ile Phe Pro Ser Phe Phe
        195                 200                 205

Asp Ile Gln Thr Lys Leu Ala Asp Glu Ala Tyr Lys Asn Gln Ser Ile
    210                 215                 220

Gly Cys Val Gly Glu Ile His Tyr Arg Leu Leu Gly Glu Val Glu Pro
225                 230                 235                 240

Ala Lys Ile Lys Ala Ile Asn Ala Leu Ala Asp Phe Ala Leu Tyr Ala
                245                 250                 255

Gly Val Gly Arg Lys Thr Thr Met Gly Met Gly Met Thr Arg Arg Ile
            260                 265                 270

Ser Lys Asp Lys Arg
        275

<210> SEQ ID NO 3
<211> LENGTH: 332
<212> TYPE: PRT
<213> ORGANISM: Microcystis aeruginosa

<400> SEQUENCE: 3
```

```
Thr Phe Leu Thr Ser Val Asp Ala Lys Phe Phe His Ser Glu Ile Pro
1               5                   10                  15

Tyr Lys Pro Met Gly Lys Tyr Val His Phe Leu Thr Ile Arg Val Thr
                20                  25                  30

Glu Ser Tyr Pro Leu Phe Gln Thr Asp Gly Glu Leu Asn Lys Ala Arg
            35                  40                  45

Val Arg Ala Gly Ile Asp Ser Lys Lys Thr Ile Ser Arg Leu Ser Met
50                  55                  60

Phe Lys Arg Lys Gln Ser Thr Pro Glu Arg Leu Val Gly Arg Glu Leu
65                  70                  75                  80

Leu Arg Asn Tyr Gly Leu Ile Thr Ala Glu Glu Cys Glu Tyr Asn Val
                85                  90                  95

Lys Phe Ala Met Asn Asn Ala Asp Cys Ile Ile Tyr Gly Phe Ala Ile
                100                 105                 110

Gly Asp Ser Gly Ser Glu Lys Ser Lys Val Val Val Asp Thr Ala Phe
            115                 120                 125

Ser Ile Thr Pro Phe Asp Glu Ser His Glu Ser Phe Thr Leu Asn Ala
            130                 135                 140

Pro Tyr Glu Asn Gly Thr Met Ala Ser Lys Gly Glu Asn Asn Thr Lys
145                 150                 155                 160

Val Gly Glu Val Thr Ser Arg Ile Asn Gln Gln Asp His Ile Arg Pro
                165                 170                 175

Gln Val Phe Phe Pro Ser Ile Val Thr Leu Lys Asp Pro Thr Glu Ala
            180                 185                 190

Ser Phe Leu Tyr Val Phe Asn Asn Ile Leu Arg Thr Arg His Tyr Gly
            195                 200                 205

Ala Gln Thr Thr Arg Thr Gly Arg Val Arg Asn Glu Leu Ile Gly Val
            210                 215                 220

Ile Phe Ala Asp Gly Glu Ile Val Ser Asn Leu Arg Trp Thr Gln Ala
225                 230                 235                 240

Ile Tyr Asp Arg Leu Pro Asp Glu Val Leu His Ser Ile Asp Pro Leu
                245                 250                 255

Asp Glu Asp Leu Val Met Glu Lys Ala Thr Glu Ala Ile Gln Ala Leu
                260                 265                 270

Met Ala Glu Glu Phe Ile Val His Thr Asp Phe Ile Gly Glu Asn Phe
            275                 280                 285

Gln Pro Leu Leu Thr Glu Val Lys Thr Leu Thr Gly Thr Glu Ala Gly
            290                 295                 300

Ile Leu Ser Val Leu Asp Gln Ala Asn Lys Glu Ser Lys Lys Tyr Phe
305                 310                 315                 320

Glu Gln Tyr Ile Glu Lys Lys Lys Ala Glu Lys Lys
                325                 330

<210> SEQ ID NO 4
<211> LENGTH: 721
<212> TYPE: PRT
<213> ORGANISM: Microcystis aeruginosa

<400> SEQUENCE: 4

Met Gly Asn Tyr Gln Val Thr Leu Lys Pro Val Tyr Ser Cys Pro Ala
1               5                   10                  15

Asp Glu Ile Pro Asp Gly Ile Lys Val Pro Gln Gly Trp Arg Leu Ser
                20                  25                  30

Trp His Gln Val Glu Thr Trp Lys Ala Leu Asn Asp Pro Asp Ile Asp
```

```
            35                  40                  45
Val Ile Phe Asn Thr Ala Met Thr Gly Asp Gly Lys Ser Leu Ala Ala
 50                  55                  60

Tyr Leu Arg Thr Leu Gln Gly Tyr Phe Pro Ile Met Gly Leu Tyr Pro
 65                  70                  75                  80

Thr Asn Glu Leu Ala Arg Asp Gln Arg Gly Gln Ile Glu Ala Tyr Ile
                 85                  90                  95

Gln Arg Phe Gln Pro Thr Asp Gln Pro Arg Val Asn Leu Leu Thr Gly
                100                 105                 110

Pro Glu Leu Glu Leu Tyr Ala Glu Arg Asp Gly Lys Thr Lys Ala Ile
                115                 120                 125

Ala Leu Glu Thr Arg Ser Lys Gln Ser Glu Ile Leu Leu Thr Asn Pro
                130                 135                 140

Asp Ile Phe His Tyr Leu His Arg Ala Ala Tyr Leu Thr Pro Tyr Asp
145                 150                 155                 160

Asn Pro Asp Gln Leu Trp Asn Arg Ile Asp Lys His Phe Asp Leu Phe
                165                 170                 175

Leu Phe Asp Glu Phe His Val Phe Gly Thr Pro Gln Val Ala Ser Ile
                180                 185                 190

Ile Asn Thr Met Leu Leu Ile Arg Arg Ala Asn Arg Gly Lys Arg Tyr
                195                 200                 205

Leu Phe Leu Ser Ala Thr Pro Asp Glu Gly Leu Leu Lys Arg Leu Asp
210                 215                 220

Lys Ala Gly Phe Arg Tyr Arg Ser Ile Asp Pro Val Arg Glu Gly Lys
225                 230                 235                 240

Tyr Arg Phe Pro Asp Thr Pro Glu Glu Ala Asn Ser Leu Ala Gln Gln
                245                 250                 255

Gly Trp Arg Gln Val Thr Ser Glu Ile Glu Leu Ser Phe Ile Pro Leu
                260                 265                 270

Pro Ser Ser Phe Gln Thr Ser Glu Asn Trp Leu Lys Glu Asn Lys Glu
                275                 280                 285

Arg Ile Leu Asp Tyr Phe Lys Arg Tyr Pro Gly Ser Lys Gly Ala Ile
                290                 295                 300

Ile Leu Asn Ser Ile Ala Ser Val Lys Arg Leu Leu Pro Ile Phe Arg
305                 310                 315                 320

Glu Leu Leu Ala Thr Ile Gly Leu Thr Val Gly Glu Asn Thr Gly Leu
                325                 330                 335

Ser Gly Thr Arg Glu Lys Leu Ala Ser Leu Asn Arg Asp Leu Val Ile
                340                 345                 350

Gly Thr Ser Thr Ile Asp Val Gly Val Asp Phe Lys Ile Asn Phe Leu
                355                 360                 365

Ile Phe Glu Ser Ser Asp Ala Gly Asn Phe Ile Gln Arg Phe Gly Arg
                370                 375                 380

Leu Gly Arg His Ser Gly Tyr Asp Arg Lys Gly Thr Ala Val Lys Phe
385                 390                 395                 400

Thr Asn Phe Thr Ala Ile Ala Leu Val Pro Lys Phe Phe Leu Glu Arg
                405                 410                 415

Leu Phe Glu Lys Lys Asp Ala Pro Leu Gln Val Gly Glu Arg Tyr Asp
                420                 425                 430

Arg Ile Gln Leu Gln Glu Ala Ile Lys Ser Asn Tyr Arg His Ile Asn
                435                 440                 445

Asn Phe Glu Gly Tyr Tyr Gln Arg Trp Gly Ala Val Gln Ser Phe Gln
                450                 455                 460
```

```
Leu Trp Trp Asn Leu Gly Ser Pro Lys Ile Lys Ser Gln Tyr Gly Glu
465                 470                 475                 480

Ser Arg Gln Lys Phe Gln Glu Cys Glu Val Phe Asp Thr Ser
                485                 490                 495

Leu Lys Arg Val Ala Gly Arg Val Lys Gly Trp Ala Asp Glu Trp Lys
            500                 505                 510

Glu Leu Ser Gly Lys Asn Gly Asn Pro Ile Phe Glu Asp Ala Ser Ser
        515                 520                 525

Phe Arg Gly Ser Ser Pro Leu Leu Cys Gly Leu Tyr Asp Ser Thr Glu
530                 535                 540

Pro Glu Glu Cys Asp Arg Phe Lys Thr Tyr Asp Leu Pro Ser Ile Leu
545                 550                 555                 560

Gly Asn Leu Glu Val Glu Val Trp Arg Lys Gly Glu Phe Lys Arg Gln
                565                 570                 575

Ile Glu Ala Thr Lys Thr Pro Ile Ala Arg Arg Phe Asp Tyr Cys
            580                 585                 590

Leu Ala Phe Leu Asn Leu Lys Gly Tyr Arg Glu Arg Leu Asn Trp
        595                 600                 605

Arg Phe Thr Tyr Asp Gly Asp Leu Gly Glu Ile Ala Ser Ala Trp Lys
610                 615                 620

Val Gln Val Leu Thr Gly Ile Gly Val Trp Gln Pro Asp Asn Pro Trp
625                 630                 635                 640

Leu Asp Arg Ile Ser Arg Glu Leu Arg Asp Leu Ala Leu Val Ser Phe
                645                 650                 655

Val Phe Ala Tyr Pro Val Ala Ala Val Arg Gln Arg Leu Gln Leu Pro
            660                 665                 670

Met His Phe Gly Ile Tyr Pro Ile Ser Asp Glu Ser Ser Leu His Ser
        675                 680                 685

Pro Leu Ser Pro Tyr Ser Ile Ala Ile Gly Gln Ala Ala Leu Leu Leu
    690                 695                 700

Asp Thr Leu Ala His Arg Phe Lys Gly Lys Gly Glu Val Trp Ile
705                 710                 715                 720

Cys

<210> SEQ ID NO 5
<211> LENGTH: 1156
<212> TYPE: PRT
<213> ORGANISM: Microcystis aeruginosa

<400> SEQUENCE: 5

Met Pro Lys Lys Gln Lys Lys Leu Glu Glu Thr Gly Gln Leu Asn Leu
1               5                   10                  15

Phe Asp Asn Thr Thr Glu Ile Asp Asp Glu Asp Leu Asp Phe Glu Phe
            20                  25                  30

Glu Asp Ile Asp Leu Glu Ser Leu Val Ser Glu Asp Leu Gly Ile Thr
        35                  40                  45

Glu Ser Val Ser Asp Arg Arg Val Glu Thr Val Arg Gln Leu Leu Thr
    50                  55                  60

Leu Lys Leu Leu Arg Glu Ala Ile Arg Ala Glu Asn Pro Asp Asp Arg
65                  70                  75                  80

Val Met Ala Asp Phe Ala Glu Met Val Leu Pro Asn Leu Leu Arg Leu
                85                  90                  95

Ala Ile Gly Val Thr Ala Lys Gly Gly Asn Phe Ile Glu Ala Val Asp
            100                 105                 110
```

```
Arg Gly Arg Glu Leu Arg Asn Lys Pro Lys Ala Lys Arg Asp Asn Ala
            115                 120                 125

Gly Asp Gln Ser Leu Asn Thr His Leu Leu Asn Gly Leu Phe Pro Ala
        130                 135                 140

Asn Leu Ile Glu Lys Arg Leu Gln Lys Leu Asn Thr Thr Val Arg Arg
145                 150                 155                 160

Ile Ile Lys Glu Phe Glu Arg Arg Leu Ala Ile Ala Gly Phe Leu Val
                165                 170                 175

His Asp Phe Glu Lys Phe Ser Tyr Asp Arg Phe Pro Ser Met Ser Glu
            180                 185                 190

Arg Tyr Ile Gln Ile Gln Arg Asp Phe Ile Gln Asp Pro Phe Lys Asn
            195                 200                 205

Gln Asp Pro Arg Lys Leu Ser Arg Glu His Arg Glu Ile Leu Gln
210                 215                 220

Val Leu Ile Pro Glu Leu Gly Leu Asp Arg Phe Leu Phe Pro Asp Asn
225                 230                 235                 240

Pro Glu Arg Trp Leu Glu Tyr Leu Asp Asp Leu Leu Tyr Ile Ala Lys
                245                 250                 255

Asn Thr Gln Arg Arg Asn Asp Thr Asp Leu Asn Thr Ser Glu Asp Gly
            260                 265                 270

Leu Asn Val Arg Leu Asn Asp Arg Val Ile Glu Ser Leu Cys Asp Leu
            275                 280                 285

Ala Cys Leu Ala Asp Arg Leu Ala Ser Ile Ile Lys His Pro His Asp
            290                 295                 300

Ala Glu Lys Ala Ser Leu Gln Asp Leu Leu Tyr Ser Leu Ser Asp Gly
305                 310                 315                 320

Glu Leu Lys Phe Thr Tyr His Ser Ile Ala Glu Asn Arg Gly Val Leu
                325                 330                 335

Thr Asn Val Leu Asn Asn Ala Val Met Glu Ala His Gln Glu Leu Asp
            340                 345                 350

Tyr Gln Pro Leu Leu Tyr Leu Pro Thr Gly Val Val Tyr Ile Ala Pro
            355                 360                 365

Lys Asn Ala Pro Glu Val Ser Leu Glu Thr Leu Pro Asn Arg Val Val
            370                 375                 380

Asp Thr Ile Lys Ser Leu Cys Ser Gly Glu Leu Gln Arg Lys Gln Thr
385                 390                 395                 400

Gly Phe Gly Arg Asp Gly Lys Gly Met Lys Tyr Ala Asp Tyr Tyr Ser
                405                 410                 415

Gln Phe Phe Asp Asp Ala Gly Leu Met Arg Ala Ala Leu Asn Ala Thr
            420                 425                 430

Leu Arg Ile Leu Gly Asp Asn Lys Ala Ser Val Ala Arg Ser Arg Gly
            435                 440                 445

Glu Asn Leu Ile Lys Phe Gln Gln Gln Gly Val Leu Pro Thr Asp Tyr
450                 455                 460

Asp Phe His Cys Glu Asp Ile Arg Ile Asp Arg Leu Ala Glu Phe
465                 470                 475                 480

Gly Asp Val Val Thr Arg Lys Ile Trp Gly Asp Arg Leu Glu Lys Ile
                485                 490                 495

Glu Gln Ala Arg Lys Leu Gln Lys Asn Leu Pro Ala Pro Asp Leu
                500                 505                 510

Asp Leu Ile Ser Glu Ile Ala His Tyr Trp Asn Leu Glu Asn Tyr Leu
            515                 520                 525
```

```
Pro Gln Ile Arg Ala Ile Lys Arg Ile Asn Glu Ser Leu Lys Glu Leu
            530                 535                 540
Lys Leu Lys Gly Asn Thr Gly Val Pro Tyr Glu Trp Tyr Tyr Leu
545                 550                 555                 560
Ala Ala Gln Tyr Leu Lys Gln His Pro Gly Ile Glu Asp Ile Arg Pro
                565                 570                 575
Val Ala Glu Asp Leu Ile Ala Phe Leu Ala Lys Ile Ala Ala Ile
            580                 585                 590
Val Ala Gly Tyr Asn Leu Pro Asp Gly Trp Glu Asp Leu Arg Glu Trp
                595                 600                 605
Val Asn Gln Val Val Gln Leu Pro Gly Arg Glu Leu Ala His Ser Ile
            610                 615                 620
Glu Thr Phe Gln Lys Glu Leu Asn His Tyr Asn Ala Ala Lys Lys Gln
625                 630                 635                 640
Gly Arg Gly Arg Gln Leu Leu Cys Ser Ile Ser His Ser Pro Tyr Ser
                645                 650                 655
Val Ser Glu Gln Met Glu Ser Ala Val Leu Phe Thr Pro Gln Val Tyr
                660                 665                 670
Thr Asn Lys Gln Met Leu Ala Gly Ser Asn Ala Lys Arg Asn Ile Ser
            675                 680                 685
Ser Ile Ala Gly Thr Glu Met Met Leu Arg Gln Ile Leu Met Asn Gln
690                 695                 700
Thr Gln Ala Val Gly Lys Arg Phe Glu Asp Gly Lys Tyr Arg Tyr Leu
705                 710                 715                 720
Tyr Phe Tyr Pro Thr Tyr Tyr Phe Thr Pro Glu Thr Asn Ser Phe Leu
                725                 730                 735
Gln Lys Ala Tyr Ala Asn Ile Ala Gln Thr Arg Phe Asp Ser Ser Ile
            740                 745                 750
Lys Leu His Phe Val Asp Lys Asn Leu Val Ala Asn Phe Asp Arg Thr
            755                 760                 765
Arg Tyr Gln Ser Val Asp Ser Phe Leu Ile Asp Glu Lys Leu Arg Gln
            770                 775                 780
Lys Lys Glu Thr Ile Asn Glu Glu Asp Gly Lys Lys Asp Arg Thr
785                 790                 795                 800
Phe Lys Leu Ser Tyr Pro Glu Asp Lys Pro Leu Thr Phe Tyr Phe Met
                805                 810                 815
Ala Leu Pro Pro Gly Arg Asn Pro Thr Asp Thr Glu Ser Trp Val Met
            820                 825                 830
Pro Ala Trp Leu Gly Leu Ala Phe Pro Met Ile Leu Asp Val Lys Thr
            835                 840                 845
Val Val Ser Glu Ser Pro Ile Pro Pro Tyr Arg Asp Gly Ala Glu Phe
850                 855                 860
Glu Glu Thr Val Phe Leu Asp Ser Ala Pro Gln Ala Ile Arg Ser Leu
865                 870                 875                 880
Thr Arg Cys Asp Arg Phe Arg Leu Asp Arg Val Leu Asn Pro Trp Gln
                885                 890                 895
Asp Asn Asp Gly Lys Lys Tyr Ser Ala Pro Leu Asn Thr Leu Thr Ala
            900                 905                 910
Ala Tyr Ser Ile His Leu Asp Val Asn Ser Lys Gln Gly Lys Thr Gly
            915                 920                 925
Tyr Asp Pro Asn Trp Gly Lys Leu Thr Glu Leu Ala Ile Asn Leu Glu
930                 935                 940
Thr Ser Pro Leu Tyr Val Phe His Tyr Phe Lys Gln Trp Lys Arg Gly
```

```
                    945                 950                 955                 960
Lys Asp Ala Asp Ile Pro Ser Ala Asn Arg Ile Ala Leu Tyr Leu Tyr
                        965                 970                 975
Asp Phe Tyr Pro Cys Phe Asp Pro Tyr Val Gln Ala Asn Arg Thr Asn
                        980                 985                 990
Leu Thr Ile Asp Met Thr Ala Glu Ser Pro Leu Asn His Pro Lys Asn
                        995                1000                1005
Leu Thr Glu Leu Tyr Arg Gln Phe Tyr Arg Ala Lys Ser Ser Lys
                    1010                1015                1020
Gly Lys Pro Ile Lys Ala Asn Ala Ile Leu Lys Pro Ile Asp Glu
                    1025                1030                1035
Ala Ala Asp Ile Ile Leu Lys Ala Asp Lys Ala Ile Ser Asp Asp
                    1040                1045                1050
Leu Thr Ser Leu Val Ala Ala Arg Leu Phe Lys Leu Met Asp Arg
                    1055                1060                1065
Val Arg Ser Gln Thr Ala Glu Gly Arg Tyr Val Ile Lys Glu Arg
                    1070                1075                1080
Asp Gln Glu Arg Glu Lys Ile Leu Asp Phe Ala Lys Tyr Phe Val
                    1085                1090                1095
Lys Asn Val Phe Glu Glu Ser Phe Glu Ser Asp Arg Ala Arg Leu
                    1100                1105                1110
Ala Gly Arg Gln Leu Asn Ile Ile Arg Asp Thr Cys Glu Phe Leu
                    1115                1120                1125
Tyr Arg Leu Glu Met Asp Lys Glu Arg Arg Gln Arg Gln Val Gln
                    1130                1135                1140
Pro Leu Asp Thr Ser Asn Ser Ser Ser Glu Glu Glu Glu
                    1145                1150                1155

<210> SEQ ID NO 6
<211> LENGTH: 109
<212> TYPE: RNA
<213> ORGANISM: Artificial
<220> FEATURE:
<223> OTHER INFORMATION: TiDcrRNA
<220> FEATURE:
<221> NAME/KEY: misc_feature
<222> LOCATION: (38)..(72)
<223> OTHER INFORMATION: n is a, c, g, or u

<400> SEQUENCE: 6
guuccaauua aucuuaagcc cuauuaggga uugaaacnnn nnnnnnnnnn nnnnnnnnnn       60
nnnnnnnnnn nnguuccaau uaaucuuaag cccuauuagg gauugaaac                  109

<210> SEQ ID NO 7
<211> LENGTH: 675
<212> TYPE: DNA
<213> ORGANISM: Artificial
<220> FEATURE:
<223> OTHER INFORMATION: Cas5d nucleotide sequence for expression in
      Escherichia coli

<400> SEQUENCE: 7
atggtgcata tttatagctg ccagctggaa ctgcatgata gcctgtatta tgcgacccgc       60
gaaattggcc gcctgtatga agcgaaccg gtgattcata actatgcgct gtgctatgcg       120
ctgggcctgg tgaacagcga tagctatcgc tatttctgca gcgaacagat tccgcagtat      180
caggaacatc tgaacccgct gaacgaagaa aaaatttatg tgaccccggc gcgcgcgatt      240
gcgcataccg cggtgctgaa cacctggaaa tatgcgaaca caactatca tgtggaaatg      300
```

```
gaaaaaaccc agaaaaacat tccgagcttc ggccgcgcga aagaaattgc gccggaaagc    360
attttcgaat gcttcattat tagccatcat ccgctgcagc tgccgaaatg gattcgcctg    420
ggcaaatgga tgagcaaagc ggaagtgaaa ctgaccgaac tgagcctgag caaacagaaa    480
gaagatctgt tcatttatcc gtatccgctg aacccgctgg atgtgatgtt cacccatcag    540
gtgattggct atgatgtgat taacatgccg ccggtgagcc tgattcgcaa cgtgcgcatg    600
cgcggcgaat attatcagat tagcgatcgc ccggatctga aaattccggc acgtctgagc    660
tatcatttcg gctaa                                                    675

<210> SEQ ID NO 8
<211> LENGTH: 834
<212> TYPE: DNA
<213> ORGANISM: Artificial
<220> FEATURE:
<223> OTHER INFORMATION: Cas6d nucleotide sequence for expression in
      Escherichia coli

<400> SEQUENCE: 8
atgccgtata gcctggtgct gaacctgacc ccgcgcagcc cgatttatcc gaacttcctg     60
accggccgcc atctgcatgc gctgttcctg accctggtga gcagcgtgga tcaggaactg    120
ggcaacattc tgcataccgc ggaagcggat aaagcgttca ccctgagccc gctgcagatg    180
cagagcggcg gcaaaaccat taacagcccg cagtggcgcc atgaacgcga aattgcgagc    240
gaaaccccgt gctggtggcg cattagcctg ctggatgatc gcctgttcgg caaactgacc    300
agcctgtggc tgaacctgaa cccgaaacag ccgtggcatc tgggcagcgc ggatctggtg    360
attaccagcg tgctggcgac cccgcagagc gtgcagccgt gggcgaacag ctgcacctat    420
cagtatctgt atgaaaacgc gagcgaaacc aaccgcgaat cgatttcct gttcgcgacc    480 ccggtgacct tccgccaggg caaattcgat agcgcgctgc cgacccgcga actggtgttc    540
aacagcctgc tgggccgctg gaaccgctat agcggcattc cgttcgatag cattgcgctg    600
gaaagcattt tcccgagctt cttcgatatt cagaccaaac tggcggatga agcgtataaa    660
aaccagagca ttggctgcgt gggcgaaatt cattatcgcc tgctgggcga agtggaaccg    720
gcgaaaatta aagcgattaa cgcgctggcg gatttcgcgc tgtatgcggg cgtgggccgc    780
aaaaccacca tgggcatggg catgacccgc cgcattagca agataaaacg ctaa          834

<210> SEQ ID NO 9
<211> LENGTH: 1002
<212> TYPE: DNA
<213> ORGANISM: Artificial
<220> FEATURE:
<223> OTHER INFORMATION: Cas7d nucleotide sequence for expression in
      Escherichia coli

<400> SEQUENCE: 9
atgaccttcc tgaccagcgt ggatgcgaaa ttcttccata gcgaaattcc gtataaaccg     60
atgggcaaat atgtgcattt cctgaccatt cgcgtgaccg aaagctatcc gctgttccag    120
accgatggcg aactgaacaa agcgcgcgtg cgcgcgggca ttgacagcaa gaaaaccatt    180
agccgcctga gcatgttcaa acgcaaacag agcaccccgg aacgcctggt gggccgcgaa    240
ctgctgcgca actatggcct gattaccgcg gaagaatgcg aatataacgt gaaattcgcg    300
atgaacaacg cggattgcat tatttatggc ttcgcgattg cgatagcgg cagcgaaaaa    360 agcaaagtgg tggtggatac cgcgttcagc attaccccgt tcgatgaaag ccatgagagc    420
```

| | |
|---|---|
| ttcaccctga acgcgccgta tgaaaacggc acgatggcga gcaaaggcga aaacaacacc | 480 |
| aaagtgggcg aagtgaccag ccgcattaac cagcaggatc atattcgccc gcaggtgttc | 540 |
| ttcccgagca ttgtgaccct gaaagatccg accgaagcga gcttcctgta tgtgttcaac | 600 |
| aacattctgc gcaccgcca ttatggcgcg cagaccaccc gcaccggccg cgtgcgcaac | 660 |
| gaactgattg gcgtgatttt cgcggatggc gaaattgtga gcaacctgcg ctggacccag | 720 |
| gcgatttatg atcgcctgcc ggatgaagtg ctgcatagca ttgatccgct ggatgaagat | 780 |
| ctggtgatgg aaaaagcgac cgaagcgatt caggcgctga tggcggaaga atttattgtg | 840 |
| cataccgatt tcattggcga aaacttccag ccgctgctga ccgaagtgaa acccctgacc | 900 |
| ggcaccgaag cgggcattct gagcgtgctg gatcaggcga caaagaaag caaaaaatat | 960 |
| ttcgaacagt atattgaaaa gaaaaaggcg gaaagaaat aa | 1002 |

<210> SEQ ID NO 10
<211> LENGTH: 2166
<212> TYPE: DNA
<213> ORGANISM: Artificial
<220> FEATURE:
<223> OTHER INFORMATION: Cas3d nucleotide sequence for expression in
      Escherichia coli

<400> SEQUENCE: 10

| | |
|---|---|
| atgggaaact atcaggtgac tcttaagcca gtgtattctt gcccagctga cgagatccca | 60 |
| gacggaatca aggtgccaca gggatggaga ctttcttggc accaggtgga gacttggaag | 120 |
| gctcttaacg acccagacat cgacgtgatc ttcaacactg ctatgactgg agacggaaag | 180 |
| tctcttgctg cttatcttag aactcttcag ggatatttcc caatcatggg actttatcca | 240 |
| actaacgagc ttgctagaga tcagagagga cagatcgagg cttatatcca gagattccag | 300 |
| ccaactgacc agccaagagt gaaccttctt actggaccag agcttgagct ttatgctgag | 360 |
| agagacggaa agactaaggc tatcgctctt gagactagat ctaagcagtc tgagatcctt | 420 |
| cttactaacc cagacatctt ccactatctt cacagagctg cttatcttac tccatatgac | 480 |
| aacccagacc agctttggaa cagaatcgac aagcacttcg accttttcct tttcgacgag | 540 |
| ttccacgtgt tcggaactcc acaggtggct tctatcatca cactatgct tcttatcaga | 600 |
| agagctaaca gaggaaagag atatcttttc ctttctgcta ctccagacga gggacttctt | 660 |
| aagagacttg acaaggctgg attcagatat agatctatcg acccagtgag agagggaaag | 720 |
| tatagattcc cagacactcc agaggaggct aactctcttg ctcagcaggg atggagacag | 780 |
| gtgacttctg agatcgagct ttcttcatc ccacttccat cttctttcca gacttctgag | 840 |
| aactggctta aggagaacaa ggagagaatc cttgactatt caagagata tccaggatct | 900 |
| aagggagcta tcatccttaa ctctatcgct tctgtgaaga gcttcttcc aatcttcaga | 960 |
| gagcttcttg ctactatcgg acttactgtg ggagagaaca ctggactttc tggaactaga | 1020 |
| gagaaacttg cttctcttaa cagagatctt gtgatcggaa cttctactat cgacgtggga | 1080 |
| gtggacttca agatcaactt ccttatcttc gagtcttctg acgctggaaa cttcatccag | 1140 |
| agattcggaa gacttggaag acactctgga tatgacagaa agggaactgc tgtgaagttc | 1200 |
| actaacttca ctgctatcgc tcttgtgcca agttcttcc ttgagagact tttcgagaag | 1260 |
| aaggacgctc cacttcaggt gggagagaga tatgacagaa tccagcttca ggaggctatc | 1320 |
| aagtctaact atagacacat caacaacttc gagggatatt atcagagatg gagagctgtg | 1380 |
| cagtctttcc agctttggtg gaaccttgga tctccaaaga tcaagtctca gtatggagag | 1440 |

```
tcaagacaga agttccagca ggagtgcgag gaggtgttcg acacttctct taagagagtg    1500
gctggaagag tgaagggatg ggctgacgag tggaaggagc tttctggaaa gaacggaaac    1560
ccaatcttcg aggacgcttc ttctttcaga ggatcttctc cacttctttg cggactttat    1620
gactctactg agccgaggga gtgcgacaga ttcaagactt atgaccttcc atctatcctt    1680
ggaaaccttg aggtggaggt gtggagaaag ggagagttca agagacagat cgaggctact    1740
aagactccaa tcgctagaag aagattcgac tattgccttg ctttccttaa ccttaaggga    1800
tatagagagg agagacttaa ctggagattc acttatgacg agatcttgg agagatcgct    1860 tctgcttgga aggtgcaggt gcttactgga atcggagtgt ggcagccaga caacccttgg    1920
cttgacagaa tctcaagaga gcttagagat cttgctcttg tgtctttcgt gttcgcttat    1980
ccagtggctg ctgtgagaca gagacttcag cttccaatgc acttcggaat ctatccaatc    2040
tctgacgagt cttctcttca ctctccactt tctccatatt ctatcgctat cggacaggct    2100
gctcttcttc ttgacactct tgctcacaga ttcaagggaa agggaggaga ggtgtggatc    2160
tgctag                                                                2166
```

<210> SEQ ID NO 11
<211> LENGTH: 3471
<212> TYPE: DNA
<213> ORGANISM: Artificial
<220> FEATURE:
<223> OTHER INFORMATION: Cas10d nucleotide sequence for expression in
      Escherichia coli

<400> SEQUENCE: 11

```
atgccaaaga agcagaagaa gcttgaggag actggacagc ttaacctttt cgacaacact      60
actgagatcg acgacgagga ccttgacttc gagttcgagg acatcgacct tgagtctctt     120
gtgtctgagg accttggaat cactgagtct gtgtctgaca aagagtggga gactgtgaga     180
cagcttctta ctcttaagct tcttagagag gctatcagag ctgagaaccc agacgacaga     240
gtgatggctg acttcgctga gatggtgctt ccaaaccttc ttagacttgc tatcggagtg     300
actgctaagg aggaaaactt catcgaggct gtggacagag aagagagct tagaaacaag     360 ccaaaggcta agagagacaa cgctggagat cagtctctta acactcacct tcttaacgga     420
cttttcccag ctaaccttat cgagaagaga cttcagaagc ttaacactac tgtgagaaga     480
atcatcaagg agttcgagag aagacttgct atcgctggat ccttgtgca cgacttcgag     540 aagttctctt atgacagatt cccatctatg tctgagagat atatccagat ccagagagac     600
ttcatccagg acccattcaa gaaccaggac ccaagaaagc tttcaagaga ggagcacaga     660
gagatccttc aggtgcttat cccagagctt ggacttgaca gattccttt cccagacaac     720 ccagagagat ggcttgagta tcttgacgac cttctttata tcgctaagaa cactcagaga     780
agaaacgaca ctgaccttaa cacttctgag gacgactta acgtgagact taacgacaga     840
gtgatcgagt cttttgcga ccttgcttgc cttgctgaca gacttgcttc tatcatcaag     900
cacccacacg acgctgagaa ggcttctctt caggacctct tttattctct ttctgacgga     960
gagcttaagt tcacttatca ctctatcgct gagaacagag gagtgcttac taacgtgctt    1020
aacaacgctg tgatggaggc tcaccaggag cttgactatc agccacttct ttatcttcca    1080
actggagtgg tgtatatcgc tccaaagaac gctccagagg tgtctcttga gactcttcca    1140
aacagagtgg tggacactat caagtctctt tgctctggag agcttcagag aaagcagact    1200
ggattcggaa gagacggaaa gggtatgaag tatgctgact attattctca gttcttcgac    1260
```

-continued

```
gacgctggac ttatgagagc tgctcttaac gctactctta gaatccttgg agacaacaag    1320
gcttctgtgg ctagatctag aggagagaac cttatcaagt tccagcagca gggagtgctt    1380
ccaactgact atgacttcca ctgcgaggac gacatcagaa tcgacagact tgctgagttc    1440
ggagacgtgg tgactagaaa gatctgggga gacagacttg agaagatcga gcaggctaga    1500
aagcttcaga gaaccttcc agctccacca gaccttgacc ttatctctga gatcgctcac    1560
tattggaacc ttgagaacta tcttccacag atcagagcta tcaagagaat caacgagtct    1620
cttaaggagc ttaagcttaa gggaaacact ggaggagtgc catatgagtg gtattatctt    1680
gctgctcagt atcttaagca gcacccagga atcgaggaca tcagaccagt ggctgaggac    1740
cttatcgctt tccttgctgc taagatcgct gctatcgtgg ctggatataa ccttccagac    1800
ggatgggagg accttagaga gtgggtgaac caggtggtgc agcttccagg aagagagctt    1860
gctcactcta tcgagacttt ccagaaggag cttaaccact ataacgctgc taagaagcag    1920
ggaagaggaa gacagcttct ttgctctatc tctcactctc catattctgt gtctgagcag    1980
atggagtctg ctgtgctttt cactccacag gtgtatacta caagcagat gcttgctgga    2040 tctaacgcta agagaaacat ctcttctatc gctggaactg agatgatgct tagacagatc    2100
cttatgaacc agactcaggc tgtgggaaag agattcgagg acgaaagta tagatatctt    2160 tatttctatc caacttatta tttcactcca gagactaact cttccttca gaaggcttat    2220 gctaacatcg ctcagactag attcgactct tctatcaagc ttcacttcgt ggacaagaac    2280
cttgtggcta acttcgacag aactagatat cagtctgtgg actcttcct tatcgacgag    2340 aagcttagac agaagaagga gactatcaac gaggaggagg acgaaagaa ggacagaact    2400 ttcaagcttt cttatccaga ggacaagcca cttactttct atttcatggc tcttccacca    2460
ggaagaaacc caactgacac tgagtcttgg gtaatgccag cttggcttgg acttgctttc    2520
ccaatgatcc ttgacgtgaa gactgtggtg tctgagtctc caatcccacc atatagagac    2580
ggagctgagt cgaggagac tgtgttcctt gactctgctc cacaggctat cagatctctt    2640
actagatgcg acagattcag acttgacaga gtgcttaacc cttggcagga caacgacgga    2700
aagaagtatt ctgctccact taacactctt actgctgctt attctatcca ccttgacgtg    2760
aactctaagc agggaaagac tggatatgac ccaaactggg aaagcttac tgagcttgct    2820 atcaaccttg agacttctcc actttatgtg ttccactatt tcaagcagtg aagagagga    2880 aaggacgctg acatcccatc tgctaacaga atcgctcttt atctttatga cttctatcca    2940
tgcttcgacc catatgtgca ggctaacaga actaacctta ctatcgacat gactgctgag    3000
tctccactta ccaccccaaa gaaccttact gagctttata gacagttcta tagagctaag    3060
tcttctaagg gaaagccaat caaggctaac gctatcctta agccaatcga cgaggctgct    3120
gacatcatcc ttaaggctga caaggctatc tctgacgacc ttacttctct tgtggctgct    3180
agacttttca gcttatgga cagagtgaga tctcagactg ctgagggaag atatgtgatc    3240
aaggagagag atcaggagag agagaagatc cttgacttcg ctaagtattt cgtgaagaac    3300
gtgttcgagg agtctttcga gtctgacaga gctagacttg ctggaagaca gcttaacatc    3360
atcagagaca cttgcgagtt ccttatatga cttgagatgg acaaggagag aagcagaga    3420 caggtgcagc cacttgacac ttctaactct tcttctgagg aggaggagta a             3471
```

<210> SEQ ID NO 12
<211> LENGTH: 35
<212> TYPE: DNA
<213> ORGANISM: Artificial

<220> FEATURE:
<223> OTHER INFORMATION: J23108 synthesis promoter

<400> SEQUENCE: 12
ctgacagcta gctcagtcct aggtataatg ctagc                                35

<210> SEQ ID NO 13
<211> LENGTH: 36
<212> TYPE: DNA
<213> ORGANISM: Artificial
<220> FEATURE:
<223> OTHER INFORMATION: Ribosomal binding sequence

<400> SEQUENCE: 13
aataattttg tttaacttta agaaggagat atacat                               36

<210> SEQ ID NO 14
<211> LENGTH: 24
<212> TYPE: DNA
<213> ORGANISM: Artificial
<220> FEATURE:
<223> OTHER INFORMATION: Terminator sequence STOP767

<400> SEQUENCE: 14
agatcctgta aaacgacggc cagt                                            24

<210> SEQ ID NO 15
<211> LENGTH: 19
<212> TYPE: DNA
<213> ORGANISM: Artificial
<220> FEATURE:
<223> OTHER INFORMATION: Terminator sequence STOP768(1)

<400> SEQUENCE: 15
cgccagggtt ttcccagtc                                                  19

<210> SEQ ID NO 16
<211> LENGTH: 19
<212> TYPE: DNA
<213> ORGANISM: Artificial
<220> FEATURE:
<223> OTHER INFORMATION: Terminator sequence TOP768(2)

<400> SEQUENCE: 16
cgccagggtt ttcccagtc                                                  19

<210> SEQ ID NO 17
<211> LENGTH: 47
<212> TYPE: DNA
<213> ORGANISM: Artificial
<220> FEATURE:
<223> OTHER INFORMATION: T7 terminator sequence

<400> SEQUENCE: 17
tagcataacc ccttggggcc tctaaacggg tcttgagggg tttttttg                  47

<210> SEQ ID NO 18
<211> LENGTH: 37
<212> TYPE: DNA
<213> ORGANISM: Artificial
<220> FEATURE:
<223> OTHER INFORMATION: CRISPR repeat sequence

<400> SEQUENCE: 18
gttccaatta atcttaagcc ctattaggga ttgaaac                              37

<210> SEQ ID NO 19
<211> LENGTH: 19
<212> TYPE: DNA
<213> ORGANISM: Artificial
<220> FEATURE:
<223> OTHER INFORMATION: T7 promoter sequence

<400> SEQUENCE: 19
taatacgact cactatagg                                              19

<210> SEQ ID NO 20
<211> LENGTH: 109
<212> TYPE: DNA
<213> ORGANISM: Artificial
<220> FEATURE:
<223> OTHER INFORMATION: crRNA expression cassette

<400> SEQUENCE: 20
gttccaatta atcttaagcc ctattaggga ttgaaacggt aataatacga ctcactatag    60
ggagaaagga tcgttccaat taatcttaag ccctattagg gattgaaac              109

<210> SEQ ID NO 21
<211> LENGTH: 581
<212> TYPE: DNA
<213> ORGANISM: Artificial
<220> FEATURE:
<223> OTHER INFORMATION: Synthesis cccdB gene expression cassette

<400> SEQUENCE: 21
aggctttaat acgactcact atagggagaa aggatccata aggaggtaa ataatgaagc    60 agcgtattac agtgacagtt gacagcgaca gctatcagtt gctcaaggca tatatgatgt   120
caatatctcc ggtctggtaa gcacaaccat gcagaatgaa gcccgtcgtc tgcgtgccga   180
acgctggaaa gcggaaaatc aggaagggat ggctgaggtc gcccggttta ttgaaatgaa   240
cggctctttt gctgacgaga acagggactg gtgaaatgca gtttaaggtt tacacctata   300
aaagagagag ccgttatcgt ctgtttgtgg atgtacagag tgatattatt gacacgcccg   360
ggcgacggat ggtgatcccc ctggccagtg cacgtctgct gtcagataaa gtctcccgtg   420
aactttaccc ggtggtgcat atcggggatg aaagctggcg catgatgacc accgatatgg   480
ccagtgtgcc ggtctccgtt atcggggaag aagtggctga tctcagccac cgcgaaaatg   540
acatcaaaaa cgccattaac ctgatgttct ggggaatata a                      581

<210> SEQ ID NO 22
<211> LENGTH: 18
<212> TYPE: PRT
<213> ORGANISM: Artificial
<220> FEATURE:
<223> OTHER INFORMATION: Nuclear localizing signal (NLS) amino acid
      sequence

<400> SEQUENCE: 22

Asp Pro Lys Lys Lys Arg Lys Val Asp Pro Lys Lys Lys Arg Lys Val
1               5                   10                  15

Ser Gly

<210> SEQ ID NO 23
<211> LENGTH: 54
<212> TYPE: DNA
<213> ORGANISM: Artificial
<220> FEATURE:
<223> OTHER INFORMATION: NLS nucleotide sequence

<400> SEQUENCE: 23
gacccaaaga agaagcggaa ggtagaccct aagaagaagc gcaaggtttc tgga            54

<210> SEQ ID NO 24
<211> LENGTH: 20
<212> TYPE: PRT
<213> ORGANISM: Artificial
<220> FEATURE:
<223> OTHER INFORMATION: Self-cleaving peptide 2A amino acid sequence

<400> SEQUENCE: 24

Gly Ser Glu Gly Arg Gly Ser Leu Leu Thr Cys Gly Asp Val Glu Glu
1               5                   10                  15

Asn Pro Gly Pro
            20

<210> SEQ ID NO 25
<211> LENGTH: 60
<212> TYPE: DNA
<213> ORGANISM: Artificial
<220> FEATURE:
<223> OTHER INFORMATION: Self-cleaving peptide 2A(1) coding sequence

<400> SEQUENCE: 25
ggctctgagg gcagaggcag cctgctgacc tgcggcgacg tggaggaaaa ccctggccct      60

<210> SEQ ID NO 26
<211> LENGTH: 60
<212> TYPE: DNA
<213> ORGANISM: Artificial
<220> FEATURE:
<223> OTHER INFORMATION: Self-cleaving peptide 2A(2) coding sequence

<400> SEQUENCE: 26
gggtctgagg gacgcggctc cctgctcacc tgtggagatg tggaagagaa cccaggcccc      60

<210> SEQ ID NO 27
<211> LENGTH: 60
<212> TYPE: DNA
<213> ORGANISM: Artificial
<220> FEATURE:
<223> OTHER INFORMATION: Self-cleaving peptide 2A(3) coding sequence

<400> SEQUENCE: 27
ggttctgaag gcagaggctc tctgctgaca tgtggggatg tggaggaaaa tcctggccct      60

<210> SEQ ID NO 28
<211> LENGTH: 60
<212> TYPE: DNA
<213> ORGANISM: Artificial
<220> FEATURE:
<223> OTHER INFORMATION: Self-cleaving peptide 2A(4) coding sequence

<400> SEQUENCE: 28
ggatccgagg gcagaggaag tctgctaaca tgcggtgacg ttgaggagaa tcccgggcca      60

<210> SEQ ID NO 29
<211> LENGTH: 820
<212> TYPE: DNA
<213> ORGANISM: Artificial
<220> FEATURE:
<223> OTHER INFORMATION: 2 x cauliflower mosaic virus 35S gene promoter
      + omega sequence

<400> SEQUENCE: 29

```
gccaacatgg tggagcacga cactctcgtc tactccaaga atatcaaaga tacagtctca    60
gaagaccaaa gggctattga acttttcaa caaagggtaa tatcgggaaa cctcctcgga   120
ttccattgcc cagctatctg tcacttcatc aaaaggacag tagaaaagga aggtggcacc   180
tacaaatgcc atcattgcga taaaggaaag gctatcgttc aagatgcctc tgccgacagt   240
ggtcccaaag atggaccccc acccacgagg agcatcgtgg aaaaagaaga cgttccaacc   300
acgtcttcaa gcaagtggga ttgatgtgaa catggtggag cacgcactc tcgtctactc    360 caagaatatc aaagatacag tctcagaaga ccaagggct attgagactt tcaacaaag    420 ggtaatatcg ggaaacctcc tcggattcca ttgcccagct atctgtcact tcatcaaaag   480
gacagtagaa aaggaaggtg gcacctacaa atgccatcat tgcgataaag gaaggctat    540 cgttcaagat gcctctgccg acagtggtcc caaagatgga cccccaccca cgaggagcat   600
cgtggaaaaa gaagacgttc caaccacgtc ttcaaagcaa gtggattgat gtgatatctc   660
cactgacgta agggatgacg cacaatccca ctatccttcg caagacccctt cctctatata   720 aggaagttca tttcatttgg agaggccggt ctagagtatt tttacaacaa ttaccaacaa   780
caacaaacaa caacaacat tacaattact atttacaatt                         820

<210> SEQ ID NO 30
<211> LENGTH: 447
<212> TYPE: DNA
<213> ORGANISM: Artificial
<220> FEATURE:
<223> OTHER INFORMATION: Arabidopsis shock protein 18.2kDa gene
      terminator

<400> SEQUENCE: 30
atatgaagat gaagatgaaa tatttggtgt gtcaaataaa aagcttgtgt gcttaagttt    60
gtgttttttt cttggcttgt tgtgttatga atttgtggct ttttctaata ttaaatgaat   120
gtaagatctc attataatga ataaacaaat gtttctataa tccattgtga atgttttgtt   180
ggatctcttc tgcagcatat aactactgta tgtgctatgg tatggactat ggaatatgat   240
taaagataag atgggctcat agagtaaaac gaggcgaggg acctataaac ctcccttcat   300
catgctattt catgatctat tttataaaat aaagatgtag aaaaaagtaa gcgtaataac   360
cgcaaaacaa atgatttaaa acatggcaca taatgaggag attaagttcg gtttacgttt   420
attttagtac taattgtaac gtgagac                                      447

<210> SEQ ID NO 31
<211> LENGTH: 97
<212> TYPE: DNA
<213> ORGANISM: Artificial
<220> FEATURE:
<223> OTHER INFORMATION: crRNA expression cassette

<400> SEQUENCE: 31
gttccaatta atcttaagcc ctattaggga ttgaaacgga gaccctcaat tgtcggtctc    60
gttccaatta atcttaagcc ctattaggga ttgaaac                            97

<210> SEQ ID NO 32
<211> LENGTH: 448
<212> TYPE: DNA
<213> ORGANISM: Artificial
<220> FEATURE:
<223> OTHER INFORMATION: Arabidopsis U6 snRNA-26 gene promoter sequence

<400> SEQUENCE: 32
```

```
aagcttcgtt gaacaacgga aactcgactt gccttccgca caatacatca tttcttctta      60 gcttttttc ttcttcttcg ttcatacagt tttttttgt ttatcagctt acattttctt       120
gaaccgtagc tttcgttttc ttcttttaa ctttccattc ggagttttg tatcttgttt       180 catagtttgt cccaggatta gaatgattag gcatcgaacc ttcaagaatt tgattgaata     240
aaacatcttc attcttaaga tatgaagata atcttcaaaa ggcccctggg aatctgaaag    300
aagagaagca ggcccattta tatgggaaag aacaatagta tttcttatat aggcccattt    360
aagttgaaaa caatcttcaa aagtcccaca tcgcttagat aagaaaacga agctgagttt    420
atatacagct agagtcgaag tagtgatt                                         448

<210> SEQ ID NO 33
<211> LENGTH: 723
<212> TYPE: DNA
<213> ORGANISM: Artificial
<220> FEATURE:
<223> OTHER INFORMATION: 2xNLS + Cas5d

<400> SEQUENCE: 33
gacccaaaga agaagcggaa ggtagaccct aagaagaagc gcaaggtttc tggagtgcac   60
atctattctt gccagcttga gcttcacgac tctctttatt atgctactag agagatcgga   120
agactttatg agtctgagcc agtgatccac aactatgctc tttgctatgc tcttggactt   180
gtgaactctg actcttatag atatttctgc tctgagcaga tcccacagta tcaggagcac  240
cttaacccac ttaacgagga gaagatctat gtgactccag ctagagctat cgctcacact  300
gctgtgctta acacttggaa gtatgctaac aacaactatc acgtggagat ggagaagact  360
cagaagaaca tcccatcttt cggaagagct aaggagatcg ctccagagtc tatcttcgag  420
tgcttcatca tctctcacca cccacttcag cttccaaagt ggatcagact ggaaagtgg   480 atgtctaagg ctgaggtgaa gcttactgag ctttctcttt ctaagcagaa ggaggacctt  540
ttcatctatc catatccact taacccactt gacgtgatgt tcactcacca ggttatcgga   600
tatgacgtga tcaacatgcc accagtgtct cttatcagaa acgtgagaat gagaggagag   660
tattatcaga tctctgacag accagacctt aagatcccag ctagactttc ttatcacttc  720
gga                                                                   723

<210> SEQ ID NO 34
<211> LENGTH: 882
<212> TYPE: DNA
<213> ORGANISM: Artificial
<220> FEATURE:
<223> OTHER INFORMATION: 2xNLS + Cas6d

<400> SEQUENCE: 34
gacccaaaga agaagcggaa ggtagaccct aagaagaagc gcaaggtttc tggaccatat    60
tctcttgtgc ttaaccttac tccaagatct ccaatctatc aaacttcct tactggaaga    120 caccttcacg ctctttttcct tactcttgtg tcttctgtgg accaggagct tggaaacatc   180
cttcacactg ctgaggctga caaggctttc actctttctc cacttcagat gcagtctgga   240
ggaaagacta tcaactctcc acagtggaga cacgagagag agatcgcttc tgagactcca   300
tgctggtgga gaatctctct tcttgacgac agactttttcg gaaagcttac ttctctttgg  360
cttaacctta acccaaagca gccttggcac cttggatctg ctgaccttgt gatcacttct   420
gtgcttgcta ctccacagtc tgtgcagcct tgggctaact cttgcactta tcagtatctt  480
```

```
tatgagaacg cttctgagac taacagagag ttcgacttcc ttttcgctac tccagtgact      540
ttcagacagg gaaagttcga ctctgctctt ccaactagag agcttgtgtt caactctctt      600
cttggaagat ggaacagata ttctggaatc ccattcgact ctatcgctct tgagtctatc      660
ttcccatctt tcttcgacat ccagactaag cttgctgacg aggcttataa gaaccagtct      720
atcggatgcg tgggagagat ccactataga cttcttggag aggtggagcc agctaagatc      780
aaggctatca acgctcttgc tgacttcgct ctttatgctg gagtgggaag aaagactact      840
atgggaatgg gaatgactag aagaatctct aaggacaaga ga                        882
```

```
<210> SEQ ID NO 35
<211> LENGTH: 1053
<212> TYPE: DNA
<213> ORGANISM: Artificial
<220> FEATURE:
<223> OTHER INFORMATION: 2xNLS + Cas7d

<400> SEQUENCE: 35
gacccaaaga agaagcggaa ggtagaccct aagaagaagc gcaaggtttc tggaactttc       60
cttacttctg tggacgctaa gttcttccac tctgagatcc catataagcc aatgggaaag      120
tatgtgcact tccttactat cagagtgact gagtcttatc acttttcca gactgacgga       180 gagcttaaca aggctagagt gagagctgga atcgactcta agaagactat ctcaagactt      240
tctatgttca agagaaagca gtctactcca gagagacttg tgggaagaga gcttcttaga      300
aactatggac ttatcactgc tgaggagtgc gagtataacg tgaagttcgc tatgaacaac      360
gctgactgca tcatctatgg attcgctatc ggagactctg atctgagaa gtctaaggtg       420 gtggtggaca ctgcttttctc tatcactcca ttcgacgagt ctcacgagtc tttcactctt      480
aacgctccat atgagaacgg aactatggct tctaagggag agaacaacac taaggtggga      540
gaggtgactt caagaatcaa ccagcaggac cacatcagac acaggtgtt cttcccatct       600 atcgtgactc ttaaggaccc aactgaggct tctttccttt atgtgttcaa caacatcctt      660
agaactagac actatggtgc tcagactact agaactggaa gagtgagaaa cgagcttatc      720
ggagtgatct tcgctgacgg agagatcgtg tctaacctta gatggactca ggctatctat      780
gacagacttc cagacgaggt gcttcactct atcgacccac ttgacgagga ccttgtgatg      840
gagaaggcta ctgaggctat ccaggctctt atggctgagg agttcatcgt gcacactgac      900
ttcatcggag agaacttcca gccacttctt actgaggtga agactcttac tggaactgag      960 gctgaatcc tttctgtgct tgaccaggct aacaaggagc taagaagta tttcgagcag       1020 tatatcgaga agaagaaggc tgagaagaag taa                                  1053
```

```
<210> SEQ ID NO 36
<211> LENGTH: 2217
<212> TYPE: DNA
<213> ORGANISM: Artificial
<220> FEATURE:
<223> OTHER INFORMATION: 2xNLS + Cas3d

<400> SEQUENCE: 36
atggacccaa agaagaagcg gaaggtagac cctaagaaga agcgcaaggt ttctggagga       60
aactatcagg tgactcttaa gccagtgtat tcttgcccag ctgacgagat cccagacgga      120
atcaaggtgc acagggatg gagactttct tggcaccagg tggagacttg gaaggctctt       180
aacgacccag acatcgacgt gatcttcaac actgctatga ctgagacgg aaagtctctt       240 gctgcttatc ttagaactct tcagggatat ttcccaatca tgggacttta tccaactaac      300
```

```
gagcttgcta gagatcagag aggacagatc gaggcttata tccagagatt ccagccaact    360
gaccagccaa gagtgaacct tcttactgga ccagagcttg agctttatgc tgagagagac    420
ggaaagacta aggctatcgc tcttgagact agatctaagc agtctgagat ccttcttact    480
aacccagaca tcttccacta tcttcacaga gctgcttatc ttactccata tgacaaccca    540
gaccagcttt ggaacagaat cgacaagcac ttcgaccttt cctttcga cgagttccac    600 gtgttcggaa ctccacaggt ggcttctatc atcaacacta tgcttcttat cagaagagct    660
aacagaggaa agagatatct tttcctttct gctactccag acgagggact tcttaagaga    720
cttgacaagg ctggattcag atatagatct atcgacccag tgagagggg aaagtataga    780 ttcccagaca ctccagagga ggctaactct cttgctcagc agggatggag acaggtgact    840
tctgagatcg agctttcttt catcccactt ccatcttctt tccagacttc tgagaactgg    900
cttaaggaga caaggagag aatccttgac tatttcaaga gatatccagg atctaaggga    960
gctatcatcc ttaactctat cgcttctgtg aagagacttc ttccaatctt cagagagctt   1020
cttgctacta tcggacttac tgtgggagag aacactggac tttctggaac tagagagaaa   1080
cttgcttctc ttaacagaga tcttgtgatc ggaacttcta ctatcgacgt gggagtggac   1140
ttcaagatca acttccttat cttcgagtct tctgacgctg gaaacttcat ccagagattc   1200
ggaagacttg gaagacactc tggatatgac agaaagggaa ctgctgtgaa gttcactaac   1260
ttcactgcta tcgctcttgt gccaaagttc ttccttgaga cttttcga gaagaaggac   1320 gctccacttc aggtgggaga gagatatgac agaatccagc ttcaggaggc tatcaagtct   1380
aactatagac acatcaacaa cttcgaggga tattatcaga gatggggagc tgtgcagtct   1440
ttccagcttt ggtggaacct tggatctcca aagatcaagt ctcagtatgg agagtcaaga   1500
cagaagttcc agcaggagtg cgaggaggtg ttcgacactt ctcttaagag agtggctgga   1560
agagtgaagg gatgggctga cgagtggaag gagctttctg gaaagaacgg aaacccaatc   1620
ttcgaggacg cttcttcttt cagaggatct tctccacttc tttgcggact ttatgactct   1680
actgagccag aggagtgcga cagattcaag acttatgacc ttccatctat ccttggaaac   1740
cttgaggtgg aggtgtggag aaagggagag ttcaagagac agatcgaggc tactaagact   1800
ccaatcgcta agaagattc gactattgc cttgcttctc ttaaccttaa gggatataga   1860
gaggagagac ttaactggag attcactttat gacggagatc ttgagagat cgcttctgct   1920 tggaaggtgc aggtgcttac tggaatcgga gtgtggcagc cagacaaccc ttggcttgac   1980
agaatctcaa gagagcttag agatcttgct cttgtgtctt tcgtgttcgc ttatccagtg   2040
gctgctgtga cacagagact tcagcttcca atgcacttcg gaatctatcc aatctctgac   2100
gagtcttctc tttcactctcc actttctcca tattctatcg ctatcggaca ggctgctctt   2160
cttcttgaca ctcttgctca cagattcaag ggaaagggag agaggtgtg gatctgc    2217
```

<210> SEQ ID NO 37  
<211> LENGTH: 3519  
<212> TYPE: DNA  
<213> ORGANISM: Artificial  
<220> FEATURE:  
<223> OTHER INFORMATION: 2xNLS + Cas10d

<400> SEQUENCE: 37

```
gacccaaaga agaagcggaa ggtagaccct aagaagaagc gcaaggtttc tggaccaaag     60
aagcagaaga agcttgagga gactggacag cttaaccttt tcgacaacac tactgagatc    120
```

```
gacgacgagg accttgactt cgagttcgag gacatcgacc ttgagtctct tgtgtctgag      180
gaccttggaa tcactgagtc tgtgtctgac agaagagtgg agactgtgag acagcttctt      240
actcttaagc ttcttagaga ggctatcaga gctgagaacc cagacgacag agtgatggct      300
gacttcgctg agatggtgct tccaaacctt cttagacttg ctatcggagt gactgctaag      360
ggaggaaact tcatcgaggc tgtggacaga ggaagagagc ttagaaacaa gccaaaggct      420
aagagagaca acgctggaga tcagtctctt aacactcacc ttcttaacgg acttttccca      480
gctaacctta tcgagaagag acttcagaag cttaacacta ctgtgagaag aatcatcaag      540
gagttcgaga gaaagacttgc tatcgctgga ttccttgtgc acgacttcga gaagttctct      600
tatgacagat tcccatctat gtctgagaga tatatccaga tccagagaga cttcatccag      660
gacccattca agaaccagga cccaagaaag cttttcaagag aggagcacag agagatcctt      720
caggtgctta tcccagagct tggacttgac agattccttt tcccagacaa cccagagaga      780
tggcttgagt atcttgacga ccttctttat atcgctaaga acactcagag aagaaacgac      840
actgacctta acacttctga ggacggactt aacgtgagac ttaacgacag agtgatcgag      900
tctctttgcg accttgcttg ccttgctgac agacttgctt ctatcatcaa gcacccacac      960
gacgctgaga aggcttctct tcaggacctt ctttattctc tttctgacgg agagcttaag     1020
ttcacttatc actctatcgc tgagaacaga ggagtgctta ctaacgtgct taacaacgct     1080
gtgatggagg ctcaccagga gcttgactat cagccacttc tttatcttcc aactggagtg     1140
gtgtatatcg ctccaaagaa cgctccagag gtgtctcttg agactcttcc aaacagagtg     1200
gtggacacta tcaagtctct ttgctctgga gagcttcaga gaaagcagac tggattcgga     1260
agagacggaa agggtatgaa gtatgctgac tattattctc agttcttcga cgacgctgga     1320
cttatgagag ctgctcttaa cgctactctt agaatccttg agacaacaa ggcttctgtg      1380 gctagatcta gaggagagaa ccttatcaag ttccagcagc agggagtgct tccaactgac     1440
tatgacttcc actgcgagga cgacatcaga atcgacagac ttgctgagtt cggagacgtg     1500
gtgactagaa agatctgggg agacagactt gagaagatcg agcaggctag aaagcttcag     1560
aagaaccttc cagctccacc agaccttgac cttatctctg agatcgctca ctattggaac     1620
cttgagaact atcttccaca gatcagagct atcaagagaa tcaacgagtc tcttaaggag     1680
cttaagctta agggaaacac tggaggagtg ccatatgagt ggtattatct tgctgctcag     1740
tatcttaagc agcacccagg aatcgaggac atcagaccag tggctgagga ccttatcgct     1800
ttccttgctg ctaagatcgc tgctatcgtg gctggatata accttccaga cggatgggag     1860
gaccttagag agtgggtgaa ccaggtggtg cagcttccag aagagagct tgctcactct      1920 atcgagactt tccagaagga gcttaaccac tataacgctg ctaagaagca gggaagagga     1980
agacagcttc tttgctctat ctctcactct ccatattctg tgtctgagca gatggagtct     2040
gctgtgcttt tcactccaca ggtgtatact aacaagcaga tgcttgctgg atctaacgct     2100
aagagaaaca tctcttctat cgctggaact gagatgatgc ttagacagat ccttatgaac     2160
cagactcagg ctgtgggaaa gagattcgag gacggaaagt atagatatct ttatttctat     2220
ccaacttatt atttcactcc agagactaac tcttccttc agaaggctta tgctaacatc      2280
gctcagacta gattcgactc ttctatcaag cttcacttcg tggacaagaa ccttgtggct     2340
aacttcgaca gaactagata tcagtctgtg gactcttcc ttatcgacga gaagcttaga      2400
cagaagaagg agactatcaa cgaggaggag gacggaaaga aggacagaac tttcaagctt     2460
tcttatccag aggacaagcc acttactttc tatttcatgg ctcttccacc aggaagaaac     2520
```

```
ccaactgaca ctgagtcttg ggtaatgcca gcttggcttg gacttgcttt cccaatgatc    2580
cttgacgtga agactgtggt gtctgagtct ccaatcccac catatagaga cggagctgag    2640
ttcgaggaga ctgtgttcct tgactctgct ccacaggcta tcagatctct tactagatgc    2700
gacagattca gacttgacag agtgcttaac ccttggcagg acaacgacgg aaagaagtat    2760
tctgctccac ttaacactct tactgctgct tattctatcc accttgacgt gaactctaag    2820
cagggaaaga ctggatatga cccaaactgg ggaaagctta ctgagcttgc tatcaacctt    2880
gagacttctc cactttatgt gttccactat ttcaagcagt ggaagagagg aaaggacgct    2940
gacatcccat ctgctaacag aatcgctctt tatctttatg acttctatcc atgcttcgac    3000
ccatatgtgc aggctaacag aactaacctt actatcgaca tgactgctga gtctccactt    3060
aaccacccaa agaaccttac tgagctttat agacagttct atagagctaa gtcttctaag    3120
ggaaagccaa tcaaggctaa cgctatcctt aagccaatcg acgaggctgc tgacatcatc    3180
cttaaggctg acaaggctat ctctgacgac cttacttctc ttgtggctgc tagacttttc    3240
aagcttatgg acagagtgag atctcagact gctgagggaa gatatgtgat caaggagaga    3300
gatcaggaga gagagaagat ccttgacttc gctaagtatt tcgtgaagaa cgtgttcgag    3360
gagtctttcg agtctgacag agctagactt gctggaagac agcttaacat catcagagac    3420
acttgcgagt tcctttatag acttgagatg gacaaggaga aagacagag acaggtgcag    3480 ccacttgaca cttctaactc ttcttctgag gaggaggag                           3519

<210> SEQ ID NO 38
<211> LENGTH: 35
<212> TYPE: DNA
<213> ORGANISM: Nicotiana benthamiana

<400> SEQUENCE: 38
tgggtggttt gtctacagca aaatatctgg cagat                                35

<210> SEQ ID NO 39
<211> LENGTH: 35
<212> TYPE: DNA
<213> ORGANISM: Nicotiana benthamiana

<400> SEQUENCE: 39
aaatttgcta ttggactctt gccagcaatg cttgg                                35

<210> SEQ ID NO 40
<211> LENGTH: 35
<212> TYPE: DNA
<213> ORGANISM: Solanum lycopersicum

<400> SEQUENCE: 40
tacctggatc tcagtctccc gaaagaggtg aggag                                35

<210> SEQ ID NO 41
<211> LENGTH: 811
<212> TYPE: DNA
<213> ORGANISM: Artificial
<220> FEATURE:
<223> OTHER INFORMATION: Cytomegalovirus enhancer + universal chicken
      beta-actin gene hybrid promoter

<400> SEQUENCE: 41
cgttacataa cttacggtaa atggcccgcc tggctgaccg cccaacgacc cccgcccatt    60
gacgtcaata gtaacgccaa tagggacttt ccattgacgt caatgggtgg agtatttacg    120
```

```
gtaaactgcc cacttggcag tacatcaagt gtatcatatg ccaagtacgc ccctattga      180 cgtcaatgac ggtaaatggc ccgcctggca ttgtgcccag tacatgacct tatgggactt    240
tcctacttgg cagtacatct acgtattagt catcgctatt accatggtcg aggtgagccc    300
cacgttctgc ttcactctcc ccatctcccc cctcccca ccccaattt tgtatttatt      360 tatttttaa ttattttgtg cagcgatggg ggcggggggg ggggggggc gcgcgccagg      420 cggggcgggg cggggcgagg ggcggggcgg ggcgaggcgg agaggtgcgg cggcagccaa    480
tcagagcggc gcgctccgaa agtttccttt tatggcgagg cggcggcggc ggcggcccta    540 taaaagcga agcgcgcggc gggcgggagt cgctgcgacg ctgccttcgc cccgtgcccc     600
gctccgccgc cgcctcgcgc cgcccgcccc ggctctgact gaccgcgtta ctcccacagg    660
tgagcgggcg ggacggcct tctcctccgg gctgtaatta gctgagcaag aggtaagggt   720
ttaagggatg gttggttggt ggggtattaa tgtttaatta cctggagcac ctgcctgaaa  780 tcacttttt tcaggttgga ccggtgccac c                                    811
```

```
<210> SEQ ID NO 42
<211> LENGTH: 223
<212> TYPE: DNA
<213> ORGANISM: Artificial
<220> FEATURE:
<223> OTHER INFORMATION: Bovine-derived growth hormone gene terminator
      sequence

<400> SEQUENCE: 42
gctgatcagc ctcgactgtg ccttctagtt gccagccatc tgttgtttgc ccctcccccg     60
tgccttcctt gaccctggaa ggtgccactc ccactgtcct ttcctaataa aatgaggaaa    120
ttgcatcgca ttgtctgagt aggtgtcatt ctattctggg gggtggggtg gggcaggaca    180
gcaaggggga ggattgggaa gagaatagca ggcatgctgg gga                      223

<210> SEQ ID NO 43
<211> LENGTH: 249
<212> TYPE: DNA
<213> ORGANISM: Artificial
<220> FEATURE:
<223> OTHER INFORMATION: Human U6 snRNA gene promoter

<400> SEQUENCE: 43
gagggcctat ttcccatgat tccttcatat ttgcatatac gatacaaggc tgttagagag     60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacacc                                                            249

<210> SEQ ID NO 44
<211> LENGTH: 35
<212> TYPE: DNA
<213> ORGANISM: Homo sapiens

<400> SEQUENCE: 44
ccagaaccgg aggacaaagt acaaacggca gaagc                                35

<210> SEQ ID NO 45
<211> LENGTH: 35
<212> TYPE: DNA
<213> ORGANISM: Homo sapiens
```

```
<400> SEQUENCE: 45
gatgtgatgg gagcccttct tcttctgctc ggact                                      35
```